United States Patent [19]

Bringi et al.

[11] Patent Number: 5,407,816
[45] Date of Patent: Apr. 18, 1995

[54] ENHANCED PRODUCTION OF TAXOL AND TAXANES BY CELL CULTURES OF TAXUS SPECIES

[75] Inventors: Venkataraman Bringi, Ithaca, N.Y.; Prakash G. Kadkade, Marlboro, Mass.; Christopher L. Prince, Ithaca, N.Y.; Barry F. Schubmehl, Ithaca, N.Y.; Eugene J. Kane, Ithaca, N.Y.; Braden Roach, Interlaken, N.Y.

[73] Assignee: Phyton Catalytic, Inc., Ithaca, N.Y.

[21] Appl. No.: 874,344

[22] Filed: Apr. 24, 1992

Related U.S. Application Data

[63] Continuation-in-part of Ser. No. 839,144, Feb. 20, 1992, abandoned.

[51] Int. Cl.⁶ .......................... C12P 17/02; C12P 15/00
[52] U.S. Cl. ....................................... 435/123; 435/41; 435/127; 435/240.4; 435/240.46; 435/240.48; 549/510; 549/511
[58] Field of Search ....................... 435/41, 123, 240.4, 435/240.46, 240.48, 127; 549/510, 511

[56] References Cited

U.S. PATENT DOCUMENTS 5,019,504 5/1991 Christen et al. .................... 435/123

OTHER PUBLICATIONS

Chemical Abstract 112:3779c vol. 112, No. 1, 01 Jan. 1990, Xu et al., "Determination of taxol in the extract of Taxus chinensis by reversed phase HPLC" abstract of Yaoxue Xuebao 1989, 24(7) 552–5.
Chemical Abstract 1162:124148n, vol. 116, No. 13, 30 Mar. 1992 Xu et al., "Determination of taxol in Taxus chinensis by HPLC method" abstract of Yaoxue Xuebao 1991, 26(7) 537–540.
Chem Abs 116:55524t vol. 16 No. 7 (Feb. 17, 1992) Jia et al "Chin Sci Bull" (1991) 36(14) 1174–7.
Chem Abs 117:8234j vol. 117 No. 1 (Jul. 6, 1992) Jia et al. "Chin Sci Bull" 1991 36 (23) 1967–9.
Chem Abs 113:208344z vol. 113 (Dec. 3, 1990) Zhang et al. "Plant Med" 1990 (56)3, 293–4.
Chem Abs 131964h vol. 115 (Sep. 30, 1991) Zhang et al. "Phytochem" (1991) 30(7) 2345–8.

Primary Examiner—Herbert J. Lilling
Attorney, Agent, or Firm—Hollie L. Baker; Hale and Dorr

[57] ABSTRACT

This invention is directed to methods for the enhanced production and recovery of taxol and taxanes by cell cultures of Taxus species.

18 Claims, 11 Drawing Sheets

| COMPOUND | DAY 25 | | | DAY 42 | | |
|---|---|---|---|---|---|---|
| | % D. W. | mg/L | % Extracellular | % D. W. | mg/L | % Extracellular |
| 10-Deacetylbaccatin III | 0.0000 | 0.00 | | 0.0000 | 0.00 | |
| Baccatin III | 0.0184 | 10.43 | 10.57 | 0.0420 | 19.83 | 14.72 |
| 7-Xylosyl-10-deacetyltaxol | 0.0127 | 7.19 | 24.62 | 0.0283 | 13.38 | 45.81 |
| 10-deacetyltaxol | 0.0122 | 6.95 | 17.37 | 0.0127 | 5.99 | 0.00 |
| Cephalomannine | 0.0000 | 0.00 | | 0.0119 | 5.60 | 86.02 |
| 10-deacetyl-7-epitaxol | 0.0081 | 4.61 | 62.42 | 0.0275 | 12.99 | 72.59 |
| Taxol | 0.0427 | 24.25 | 70.95 | 0.3244 | 153.34 | 87.52 |
| 7-Epitaxol | 0.0122 | 6.92 | 84.61 | 0.0154 | 7.26 | 85.28 |
| TOTAL-Unknown | 0.0452 | 25.67 | | 0.1625 | 76.83 | |
| TOTAL Taxanes | 0.1515 | 86.84 | | 0.6245 | 295.23 | |

FIG. 5A

ENHANCED PRODUCTION OF TAXOL AND TAXANES BY CELL CULTURES OF TAXUS SPECIES

This invention was made with government support under grants ET-2(AHR-8) and R43 CA55456-01 awarded by the National Institutes of Health. The government has certain rights in the invention.

This is a continuation-in-part application of application Ser. No. 07/839,144, filed Feb. 20, 1992, now abandoned.

BACKGROUND OF THE INVENTION

1. Field of the Invention

This invention is directed to methods for the enhanced production and recovery of taxol and taxanes by cell cultures of Taxus species.

2. Related Art

THE TAXOL SUPPLY PROBLEM AND POSSIBLE SOLUTIONS

Taxol is a diterpenoid alkaloid originally isolated from the bark of the pacific yew, Taxus brevifolia (Wani et al. 1971).

Interest in taxol began when the National Cancer Institute (NCI), in a large-scale screening program, found that crude bark extracts exhibited anti-tumor activities. Since then, clinical trials have confirmed that taxol is extremely effective against refractory ovarian cancers, and against breast and other cancers. Taxol has been pronounced as a breakthrough in chemotherapy because of its fundamentally different mechanism of cytotoxicity, i.e., by inhibiting depolymerization of microtubules (see Rowinsky et al. 1990).

The most daunting variable in the taxol equation so far is supply. It takes three to six 100 year old Pacific yews to treat one patient because average yields of taxol are low-ca. 0.01% of dry bark and needles (Witherup et al. 1990). To produce the amount of taxol that is needed for treatment and testing would require the destruction of tens of thousands of yews. Thus far, all of the world's supply has come from harvesting these squat, slow growing conifers that populate the ancient forests of the Pacific Northwest. Unfortunately, the yew has been rendered nearly extinct by logging. Conservationists are successfully opposing any large scale sacrificing of the tree, which grows in the ancient forest that are refuge to the endangered Northern spotted owl and other wildlife. As the number of Pacific yews dwindles, medical research is pinning its hopes for future taxol on new, alternative sources of supply. Three sources that have been considered are chemical synthesis, semi-synthesis and plant cell culture.

Taxol is a large, structurally complex chemical molecule that has thus far eluded total chemical synthesis. Therefore, large-scale synthesis from simple available chemicals is not likely to be a feasible option for the next few years.

A possible option for large-scale production is semi-synthesis, i.e., chemical attachment of a side chain to the agriculturally produced taxol precursor, 10-deacetylbaccatin. Significant progress has been made on the synthesis of the side chain (Denis et al. 1991). Methods have also been developed to couple the side chain to 10-deacetylbaccatin (Denis et al. 1990, U.S. Pat. No. 4,924,011; Holton 1991, U.S. Pat. No. 5,015,744). However, the agricultural supply of 10-deacetylbaccatin from needles of Taxus plantations is by no means trivial; and is currently being re-evaluated in light of the fact that earlier reports (Denis et al., 1988, 0.1% by weight) were more optimistic about 10-deacetylbaccatin content than recent ones (Witherup et al. 1990, 0.03% dry weight). In summary, the ability of chemical synthesis and semi-synthesis to supply taxol for world-wide chemotherapeutic use is not assured. There are strong reasons for exploring and developing alternative means of production.

This invention is related to the development of a plant cell culture-based process for the supply of taxol and other taxanes.

TISSUE CULTURES AS A SOURCE OF PLANT-DERIVED CHEMICALS

The ability of plant cells to divide, grow, and produce secondary metabolites under a variety of different cultural regimes has been amply demonstrated by a number of groups. At present, two compounds, shikonin (a red dye and anti-inflammatory) and ginsengoside (a tonic in oriental medicine) are produced by tissue-culture processes in Japan. Many other processes are reportedly close to commercialization, including vanillin, berberine and rosmarinic acid (see Payne et al. 1991).

The advantages of a plant cell culture process for taxol are many: (i) A cell culture process ensures a limitless, continuous and uniform supply of product, and is not subject to pests, disasters and seasonal fluctuations, (ii) cell cultures can be cultivated in large bioreactors, and can be induced to overproduce taxol by manipulating environmental conditions, (iii) cell cultures produce a simpler spectrum of compounds compared tobark or needles, considerably simplifying separation and purification, (iv) a cell culture process can adapt quickly to rapid changes in demand better than agriculture-based processes, (v) besides supplying taxol, a cell culture process could also produce taxane precursors such as baccatin that could be converted semi-synthetically into taxol and other active derivatives.

Since aseptic, large-scale, plant cell cultivation is inherently expensive, a cell culture process becomes commercially relevant only when these costs are offset by rapid cell growth and high metabolite productivity. Every plant species and target metabolite is different, and different approaches are necessary for every particular system. This invention focuses on creative and skilled approaches for obtaining rapidly growing and highly productive plant cell cultures for taxol and taxane production.

PROBLEMS WITH TISSUE CULTURES OF WOODY PLANTS AND CONIFERS

A historical survey of the literature suggests that whereas herbaceous plants have been relatively easily manipulated in culture, cultures of woody plants and conifers have been achieved only with difficulty.

The growth of secondary metabolite producing gymnosperm- and conifercultures have been generally low. For example, Berlin and Witte (1988) found that cultures of Thuja occidentalis increased their biomass by only ca. 30% in 18 days. Van Uden et al. (1990) reported a biomass increase of 20–50% in 21 days for suspensions of Callitris drummondii. Westgate et al. (1991) reported a doubling time of ca. 10 days for suspensions of the gymnosperm, Cephalotaxus harringtonia. As summarized by Bornman (1983), a tremendous amount of effort has been directed towards medium development for spruce suspensions (*Picea abies*). This collective work demonstrates that gymnosperm suspensions are indeed capable of rapid growth, but that no generalities can be applied, and that media formulations for different cell lines must be optimized independently.

A survey of secondary metabolite productivity among gymnosperm cultures also points to the difficulty of inducing rapid biosynthesis compared to herbaceous species. For example, cultures of *Cephalotaxus harringtonia* produced terpene alkaloids at a level of only 1% to 3% of that found in the parent plant (Delfel and Rothfus 1977). Even upon successful elicitation, Heinstein (1985) was only able to approach the levels produced in the parent plant (ca. 0.04% dry weight total alkaloids). Van Uden et al (1990) were able to induce suspension cultures of the conifer *Callitris drummondii* to produce podophyllotoxin, but only at levels one tenth of that produced by the needles. The ability of *Thuja occidentalis* to produce significant levels of monoterpenes (10–20 mg/L) and the diterpenoid dehydroferruginol (2–8 mg/L) has been convincingly demonstrated by Berlin et al. (1988). However, these results were obtained with a slow-growing (30% biomass increase in 18 days) and low cell density (5 to 7 grams dry weight per liter) culture.

CELL CULTURE FOR TAXOL PRODUCTION: PREVIOUS EFFORTS

The difficulties in achieving rapid growth and high productivity encountered in gymnosperm-suspensions have been reflected in the three reports so far on taxol production. Jaziri et al. (1991) recently initiated callus cultures of *Taxus baccata*, but were unable to detect any taxol using their immunosorbent assay. Wickremesinhe and Arteca (1991) reported the presence of 0.009% dry weight taxol in callus cultures of *Taxus media* (cv. hicksii), but details on the doubling times, cell densities, and the time-scale over which the reported taxol was produced, were not indicated.

U.S. Pat. No. 5,019,504 (Christen et al. 1991) describes the production and recovery of taxane and taxane-like compounds by cell cultures of *Taxus brevifolia*. These workers reported taxol production at a level of 1 to 3 mg/L in a two- to four-week time frame. They also reported a cell mass increase of "5–10 times in 3–4 weeks", which corresponds to doubling times of ca. 7 to 12 days.

Increases in growth rates, taxol biosynthesis rates, and volumetric productivities are clearly necessary before a tissue culture process for taxol production can supply the projected annual demand of tens to hundreds of kilograms of taxol per year.

SUMMARY OF THE INVENTION

The inventors have discovered that taxol and taxol-like compounds, or taxanes, can be produced in very high yield from all known *Taxus* species, i.e., *brevifolia, canadensis, cuspidata, baccata, globosa, floridana, wallichiana, media* and *chinensis*. In particular, the inventors found that the species, *Taxus chinensis*, is capable of rapid growth and of producing extremely high levels of taxol and taxanes within a short period of time.

Improving upon the invention described in Christen et al. (1991), the inventors herein have discovered that cell cultures from different *Taxus* species can be rapidly and efficiently initiated, and successfully grown on artificial nutrient media and that the same chemotherapeutically active taxane alkaloids are produced in the cell culture as in the intact plant.

Further, by the methods of this invention it is possible to obtain taxol in a much shorter time frame than previously reported. With the species *Taxus chinensis*, the inventors have been able to manipulate cells to yield taxol in amounts far in excess of the amounts obtained from tissue cultures of the other *Taxus* species. Moreover, the growth rate of the *Taxus chinensis* cell cultures is significantly higher, 3 to 6 fold, than for *Taxus brevifolia* described in Christen et al. (1991).

The objects of this invention include the rapid and efficient initiation of cell cultures from various species of *Taxus*.

The objects of this invention include the formulation of special environmental conditions to foster rapid growth, high cell densities, and high cell viabilities. The growth characteristics reported in this study surpass previous results by a significant factor.

The objects of this invention include the ability to induce high and prolonged rates of taxol and taxane biosynthesis and secretion by: (a) careful manipulation of nutrient concentrations ('production medium formulation'), (b) use of light, (c) use of periodic medium exchange protocols, (d) use of elicitors.

The objects of this invention include the ability to manipulate the profile of taxanes produced by altering media formulations and environmental conditions. In particular, cells were coaxed to produce taxol as the predominant taxane product. In addition, the production of the by-product cephalomannine was suppressed, thereby providing an elegant biological solution to an expensive and important downstream separation and purification problem.

The objects of this invention include the ability to produce various taxanes other than taxol that might themselves show pharmacological activity, or may be modified and converted to compounds with pharmacological activity.

The objects of this invention include the ability to induce cell cultures of *Taxus chinensis* to produce taxol (0.32% dry weight) at levels far exceeding those produced in wild plants (0.003 to 0.03% dry weight, Xu and Liu 1991).

DESCRIPTION OF THE FIGURES

FIG. 6A shows the ion spray APCI mass spectrum of authentic taxol and panel FIG. 6B shows the daughter ion spectrum of the parent peak (m/z871=taxol+$NH_4^+$). Panel FIG. 6C represents the ion spray APCI spectrum from a crude cell culture extract and shows m/z 854 and 871 characteristic of taxol. Panel

DETAILED DESCRIPTION OF THE INVENTION

Figure 1:
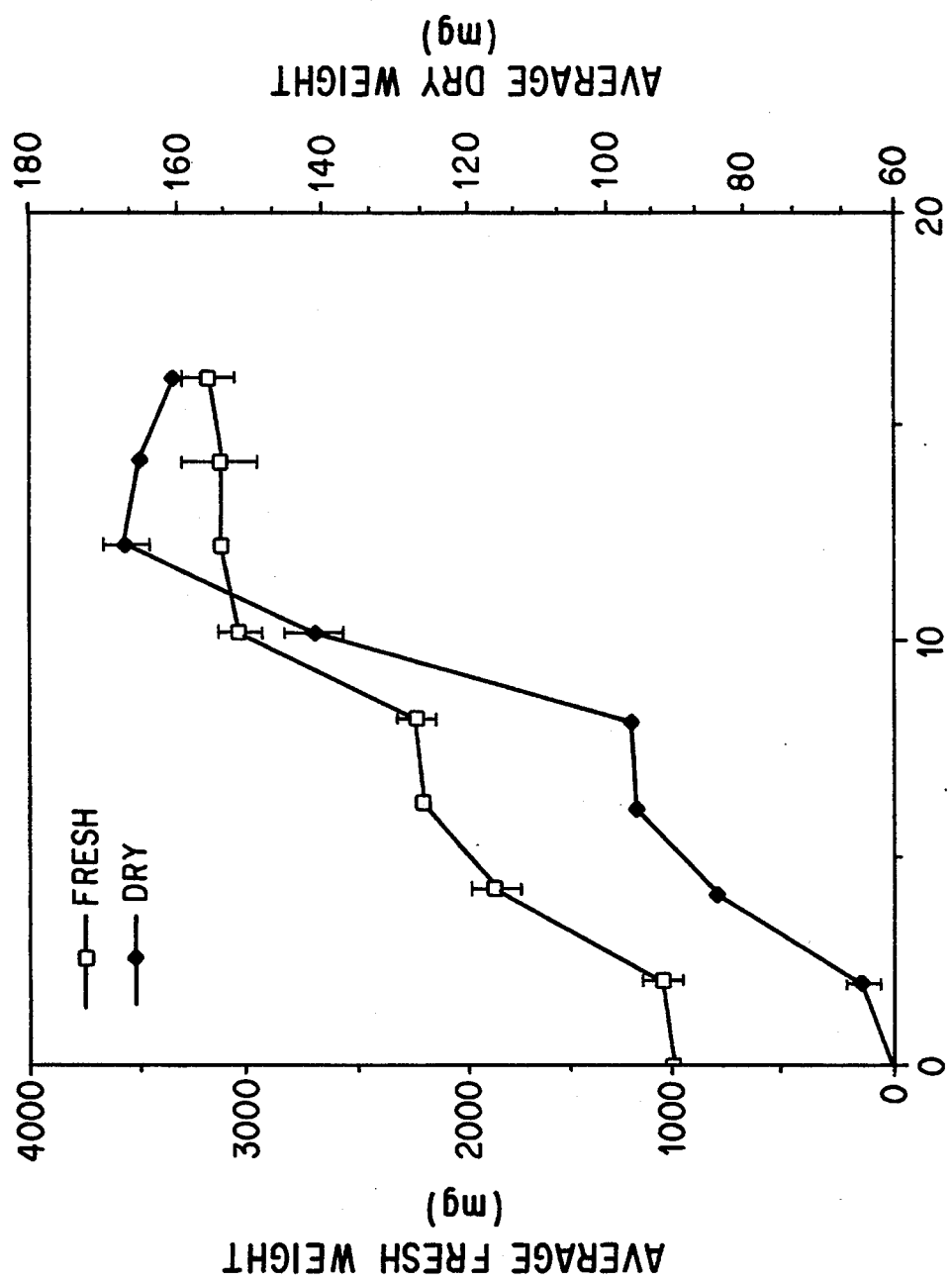
FIG. 1. Biomass increase in a *Taxus chinensis* suspension culture line K-1 over a typical batch growth cycle in Medium A. Error bars represent the standard deviation measured from duplicate flasks.

Plants have long provided important sources of pharmaceuticals and specialty chemicals. These products have typically been obtained through extraction of the harvested plant materials or by chemical synthesis. Taxol has become one of the most important potential anticancer agents to recently emerge from the screening of natural products.

As used herein, the terms taxol and taxol-like compounds, or taxanes, are used interchangeably to describe a compound with a taxane ring. These compounds may themselves possess antineoplastic activity, or may be modified to yield bioactive compounds.

As used herein, the term "callus" is used to describe a mass of cultured plant cells that is structurally undifferentiated, and is cultivated on solidified medium. As used herein, the term "suspension culture" is used to describe structurally undifferentiated cells that are dispersed in a liquid nutrient medium. It is understood that suspension cultures comprise cells in various stages of aggregation. A range of aggregate sizes are encountered in the suspensions described in this invention, with sizes ranging from tens of microns in diameter (single cells or few-aggregated cells) to aggregates many millimeters in diameter, consisting of many thousands of cells.

The plant material useful in this invention was obtained from all known Taxus species, i.e., *brevifolia, canadensis, cuspidata, baccata, globosa, floridana, wallichiana, media* and *chinensis*. In particular, the inventors have identified the species *Taxus chinensis* as capable of producing significant quantities of taxol and taxanes in a short period of culture time, with desired compounds being secreted continuously into the medium.

It has been found by the inventors that specific taxol content varies with plant species, and within plant species from tissue source and specific trees. Selecting a high yielding source for taxol production is an important first step towards providing sufficient quantities of taxol for therapeutic use.

INITIATION OF *TAXUS* CELL LINES

*Taxus* plant material may be collected from all over North America as well as from other continents. The culture is initiated by selecting appropriate *Taxus* tissue for growth. Tissue from any part of the plant, including the bark, cambium, needles, stems, seeds, cones, and roots, may be selected for inducing callus. However, for optimum yield of taxol, needles and meristematic regions of plant parts are preferred. Most preferred are new growth needles (e.g., one to three months old), which can generally be identified by a lighter green color. The term "new growth" is broadly intended to mean plant needle production within that year's growing season.

To prevent contamination of the culture, the tissue should be surface-sterilized prior to introducing it to the culture medium. Any conventional sterilization technique, such as "Chlorox" (a trademark owned by the Chlorox Company for bleach) treatment would be effective. In addition, antimicrobial agents such as cefoxitin, benlate, cloxacillin, ampicillin, gentamycin sulfate, and phosphomycin may be used for surface sterilization of plant material.

CALLUS GROWTH

Cultures will typically exhibit variability in growth morphology, productivity, product profiles, and other characteristics. Since individual cell lines vary in their preferences for growth medium constituents, many different growth media may be used for induction and proliferation of the callus.

The appropriate medium composition varies with the species being cultured. The preferred media for the different species are listed in Table 3. For example, although others may be used, the two preferred growth nutrient media for *Taxus chinensis* are A & D. These media preferably contain the ingredients listed in Table 2. For example, when A medium is used, growth hormones or regulators incorporated into the medium in an amount between 1 ppb to 10 ppm, and preferably at 2 ppb to 1 ppm. When medium D is used, the growth hormones or regulators are incorporated at levels ranging from 1 ppb to 10 ppm, and preferably at 2 ppb to 2 ppm. The amounts of other medium ingredients can be incorporated at levels ranging from 1/10th concentration to three times the concentrations indicated in Table 2, but are preferably incorporated at the levels shown in Table 2.

SUSPENSION GROWTH

*Taxus* suspension cultures are capable of rapid growth rates and high cell densities like other plant cell cultures. However, optimal conditions vary from one cell line to another, and accordingly, methods leading towards rapid optimization for any given cell line must be considered.

The initial cultures of various *Taxus* species are subcultured by transfer into the media listed in Table 3, containing macro and micronutrients, organic salts and growth hormones. The amounts are generally with the following ranges: starting with 1/10th concentration to three times the concentration of each medium ingredient shown in Table 2. The preferred levels are those listed in Table 2.

The liquid cultures are exposed to air and preferably shaken or otherwise gently moved to introduce air into the medium, or air may be introduced through tubing into the culture vessels. The cultures are maintained under appropriate growth conditions at a temperature between 20° to 26° C. The pH may be from about 3 to 7 and preferably between 4 to 6. The culture may be grown under light conditions ranging from total darkness to total light (narrow band and/or broad spectrum) for various periods of time. Because total taxol production is highest in cultures exposed to light, this is preferred. Typical light intensity conditions range between about 100 to about 3000 foot candle power.

The suspension cultures are maintained for 1 to 8 weeks from the time of subculturing, after which culture growth declines. The cultures are harvested by removal of the growth medium, as by filtration. The harvested culture is weighed and dried, as by lyophilization, ground to a fine powder, and the taxol may be extracted by use of conventional solvent extraction techniques.

Doubling times have been measured by monitoring time-dependent biomass increase, as well as by simply monitoring the growth index during routine subculture. Maximum dry weight densities of 15-24 grams per liter have been achieved. The growth characteristics of various Taxus species suspensions are elaborated in Example 4.

ANALYTICAL METHODS

Methods for the extraction and recovery of taxol and taxanes from cells and the medium follow conventional techniques and are described in detail in Example 5. The immuno-assay (ELISA) technique largely followed the protocols supplied by Hawaii Biotechnology in the commercially available kit. High performance liquid chromatography methods were slightly modified from existing protocols as elaborated in Example 5. Under the conditions used in this invention, clear resolution of taxane peaks was achieved, resulting in accurate detection and quantitation. Because of the possibility of co-eluting non-taxane components, the spectral purity of every putative taxane peak was checked by diode array before integration of peak areas. Retention times of taxane standards are listed in Example 5, and a sample chromatogram is included in FIG. 4.

PRODUCTION MEDIUM CONDITIONS

As used herein, the term "nutrient medium" is used to describe a medium that is suitable for the cultivation of plant cell callus and suspension cultures. The term "nutrient medium" is general and encompasses both "growth medium" and "production medium". The term "growth medium" is used to describe an nutrient medium that favors rapid growth of cultured cells. The term "production medium" refers to a nutrient medium that favors taxol and taxane biosynthesis in cultured cells. It is understood that growth can occur in a production medium, and that production can take place in a growth medium; and that both optimum growth and production can take place in a single nutrient medium.

Certain classes of additives in the nutrient medium are referred to by special names in this invention, and are defined here. As used herein, the term "anti-browning agents" refer to components that are added to the nutrient medium to prevent the formation of pigments during cell cultivation. These pigments include phenolics and related compounds that are generally observed to have a deleterious effect on cell growth, viability, and product formation. As used herein, the term "biosynthetic precursors" are used to describe compounds added to the nutrient medium that are metabolized and incorporated by the cells into taxol and taxanes. As used herein, the term "metabolic inhibitors" are used to describe compounds added to the nutrient medium that interfere with specific biosynthetic pathways. For example, a metabolic inhibitor may be used to enhance taxol biosynthesis by blocking a different pathway that competes with taxol for an early biosynthetic precursor.

As used herein, the term stimulator or activator is used to describe compounds added to the nutrient medium that stimulate or activate specific biosynthetic pathways, for example those leading to taxol biosynthesis. It is understood that the mechanism of action of the additives described herein may not be completely understood.

If secondary metabolite formation in a suspension culture takes place concurrently with growth, the metabolite is termed growth-associated, and a single medium formulation may be sufficient to achieve good growth and high level production. In many other systems, it has been found that rapid growth and high product formation do not take place concurrently. In such cases, growth and production phases are separated and a medium for each phase is developed independently (reviewed in Payne et al. 1991). In the case of taxol and taxane production in *Taxus chinensis*, growth and rapid product formation have been separated, and independent media have been developed for each. However, it is understood that a single growth/production medium may be formulated for this culture. The production media developed here not only increase total taxol and taxane formation, but also direct cellular biosynthesis towards taxol production. In addition, production of interfering by-products such as cephalomannine is minimal compared to bark tissue. The production media developed here also promote prolonged cell viability and biosynthesis, and in addition, cause significant levels of product to be secreted into the extracellular medium. These characteristics are extremely important in the operation of an efficient commercial scale process for taxol production.

Although others may be used, the preferred production media for the various species are listed in Table 5. For example, although others may be used, the preferred production media for *Taxus chinensis* are B & C. These media preferably contain the ingredients listed in Table 2. These media preferably contain major and minor inorganic salts, organics and growth hormones or growth regulators. The amounts are generally with the following ranges starting with the 1/10th to three times the concentration of each medium ingredient indicated in Table 2. However, the preferred levels are those listed in Table 2.

Where medium B is used, the growth regulators are incorporated into the medium in an amount between 0.1 ppm to 20 ppm, and preferably between 1 ppm to 10 ppm. When Medium C is used, the growth regulators are incorporated preferably at levels ranging from 0.1 ppm to 5 ppm.

It is understood that modifications may be made in this medium such as substitution of other conventional salt compositions (such as organics, vitamins, amino acids, precursors, activators and inhibitors), addition or deletion of various components, growth regulators or alteration of proportions.

In addition to non-volatile dissolved nutrients, gaseous components, primarily oxygen, carbon dioxide, and ethylene (a plant hormone), play critical roles in growth and product formation. Two parameters are important. The dissolved gas concentrations favoring growth and taxol formation are obviously important since they dictate reactor operating conditions. In addition, the rates of consumption or production need to be incorporated into reactor design, so that the optimum specified concentrations can be maintained.

Besides its importance in respiration, oxygen can also dramatically affect the rate of secondary biosynthesis. A high saturation constant for an oxygen-requiring step on a secondary biosynthetic pathway may require cells to be subjected to high oxygen levels in the reactor. The importance of $CO_2$ supplementation in maintaining high growth rates has been documented. Ethylene, a plant hormone, plays pleiotropic roles in all aspects of plant growth and development, including secondary metabolism (e.g., see Payne et al., 1991 ).

ELICITORS

In order to improve the yield of taxol and other related taxanes in cell cultures, the inventors have undertaken a number of approaches. One of the approaches that has been used to enhance productivity is the use of so-called elicitors. As used herein, the term elicitors is used for compounds of biological and non-biological origin that cause an increase in secondary metabolite production when applied to plants or plant-cell cultures (Eilert 1987; Ebel 1984; and Darvill et al. 1984). Many different compounds can act as elicitors, depending upon their nature of origin and their mode of action with cell metabolism. In these studies, the inventors have used two major kinds of elicitors: 1) Biotic elicitors which usually comprise cell wall extracts or filtrates from a selected group of fungi, bacteria and yeasts, and also their purified fractions. 2) Abiotic elicitors which have included chemical stress agents as well as some compounds of biological origin (see elicitors listed in Table 1).

Christen et al.(1991) report the use of fungal elicitors and selected compounds for production of taxol by suspensions of *Taxus brevifolia;* however, the increases in the level of taxol accumulation due to elicitor treatments have not been specified.

In general, both kinds of elicitors were effective, although the extent to which elicitation (taxane accumulation in cell cultures as well as their secretion into the medium) occurred differed from elicitor to elicitor and from species to species. The highest production increase was attained with chitosan glutamate, lichenan, ferulic acid and benzoic acid. Chitosan and lichenan are complex polysaccharides derived from microbial cell walls. Chitosan when used alone is insoluble in medium, and is toxic and causes permanent cell damage. Chitosan glutamate, on the other hand, is readily soluble in medium and does not affect cell viability. Ferulic and benzoic acids are synthesized chemicals of biological origin, and are generally used as anti-oxidants in biological systems.

Elicitors interact with dissolved gases in many ways. Oxygen requirements may change upon elicitation. Increases in respiration rates as a wound response is commonly observed in plant cell cultures. Importantly, elicitors may mediate their action via ethylene. In such cases, it may be desirable to substitute a microbial elicitor preparation with ethylene, and perhaps prevent toxicity associated with other microbial components in the elicitor preparation.

Elicitors and metabolic stress agents may be utilized according to this invention to maximize taxol production and secretion in tissue culture by assessing elicitor specificity and concentration, timing, and duration, as a function of culture age and media composition.

RAPID MEDIUM EXCHANGE FOR PRODUCTIVITY ENHANCEMENT

As documented in Example 7.3., the removal of spent medium and replenishment of fresh medium every 3 days contributed to significant enhancement of total taxane and taxol production, as well as to an increase in the amounts of extracellular product.

The stimulatory effects of medium exchange may have been due to removal of product in situ, which would prevent feedback inhibition and product degradation. Such positive effects of in situ product removal on secondary metabolite production and secretion in suspension cultures have been documented by, among others, Robins and Rhodes (1986) and Asada and Shuler (1989). The periodic removal of spent medium incorporates the above advantages, and additionally, may serve to derepress secondary biosynthesis by removing other, non-taxane, inhibitory components (such as phenolic compounds) from the medium.

The replenishment of fresh medium to cells undergoing active biosynthesis may also enhance production by providing essential nutrients that have been depleted. For example, Miyasaka et al. (1986) were able to stimulate stationary phase cells of *Salvia miltiorhiza* to produce the diterpene metabolites, cryptotanshinone and ferruginol simply by adding sucrose to the medium. Presumably, biosynthesis had ceased due to carbon limitation in the stationary phase. The periodic-medium-exchange protocol used in the present work could have been beneficial as a result of any of the above factors.

It is understood that the amount of medium exchanged, the frequency of exchange, and the composition of the medium being replenished may be varied.

The ability to stimulate biosynthesis and secretion by periodic medium exchange has important implications for the design and operation of an efficient commercial process in the continuous, semi-continuous or fed-batch mode.

LIGHT

For higher plants, light is a potent factor in secondary metabolism both in intact plant as well as in cell cultures. Both the intensity and wavelength of light are important (Seibert and Kadkade 1980). For example, flavanoid and anthocyanin biosynthesis are usually favored by high intensity continuous light, while dark-cultivated cultures may be preferable for other metabolites. Increase in greening or photosynthetic capacity of cultured cells may also increase product formation or product spectrum. The inventors' studies involved the use of broad-band and well as specific narrow-band light sources. As shown in Example 7.3., light exposure can bring about increased taxol accumulation as well as secretion into the medium. The stimulatory effect of light on taxol production suggests the existence of unique control mechanisms for biosynthesis of taxanes. The nature of the photoreceptor and biochemical characteristics of light-induced stimulation are not yet clear.

MODES OF PROCESS OPERATION

The operating mode for a plant cell culture process refers to the way that nutrients, cells and products are added or removed with respect to time (Payne et al. 1991). When all the nutrients are supplied initially, and the culture contents comprising cells and product are harvested at the end of the culture period, the operating mode is termed a "one-stage batch process". When a batch process is divided into two sequential phases, a growth and a production phase, with the medium being exchanged in between the two phases, the operating mode is termed a "two-stage batch process".

In a "fed-batch" operation, particular medium additives and nutrients are supplied either periodically or continuously through the course of a one-stage or a two-stage batch culture.

When a substantial portion, but not all, of the contents of a batch culture is harvested, with addition of fresh medium for continued cell growth and production, the process resembles a "repeated draw and fill" operation, and is termed a "semi-continuous process".

When fresh medium is continuously supplied, and effluent medium is continuously removed, the process is termed "continuous". If cells are retained within the reactor, the process is termed a "perfusion mode" If cells are continuously removed with the effluent medium, the continuous process is termed a "chemostat".

It is understood that these various modes of process operation are compatible with the taxol-production system described herein.

EXAMPLES

The following examples further describe the Materials and Methods used in carrying out the invention. The examples are intended to be illustrative and are not intended to limit the invention in any manner.

The *Taxus chinensis* lines K-1 has been placed on deposit at the American Type culture Collection (ATCC) located at 12301 Parklawn Drive, Rockville, Md., USA, under deposit accession number ATCC 75817 on Jun. 22, 1994.

Example 1

Callus Initiation

Samples of *Taxus* plant material were collected from a number of wild and cultivated plants. Samples were processed upon arrival at the laboratory or stored at 4° C. until they could be used.

The material was first washed in dilute soap solution, rinsed in water, and the surface sterilized in a Chlorox solution (1% hypochlorite, pH 7) for 10 minutes. Under sterile conditions the material was then rinsed 3 times with sterile water. Needles were then cut in a 1% polyvinylpyrrolidone (PVP) solution with 100 mg/l ascorbic acid. Needles were placed with the cut end in Medium E (see Table 2). Thirty to forty explants were cultured per plate of medium. Plates containing explants were incubated at 24°±1° C. in the dark. Plates were monitored daily for the appearance of contaminating micro-organisms, and where they were present, uncontaminated needles were removed and placed in a fresh plate of Medium E. Substantial callus formation was observed and the callus was separated from the explant by 20 days and placed on the various callus proliferation media listed in Table 3. For example, calli of *Taxus chinensis* were transferred to Medium D (see Table 2). This initiation procedure was very efficient, resulting in low contamination rate and high frequency of callus induction of over 90% of explants initiated. The same procedure was successfully used to initiate cultures of *Taxus brevifolia, Taxus canadensis, Taxus cuspidata, Taxus baccata, Taxus globosa, Taxus floridana, Taxus wallichiana, Taxus media,* and *Taxus chinensis*.

Example 2

Callus Proliferation

Once calli were removed from the explant, they are cultivated at 24°+1° C. in the dark. Healthy parts of the callus were transferred to fresh medium every 10 days, and this frequency of transfer was found to be extremely important for prevention of browning and for prolonged callus maintenance. The preferred growth and maintenance media for calli of various species are summarized in Table 3.

Example 3

Suspension Initiation 1 g fresh weight of callus material was aseptically inoculated into a 125 ml Erlenmeyer flask containing 25 ml of liquid medium appropriate to each species (see Table 3). For example, Medium D was used for *Taxus chinensis*. The flask was covered with a silicone foam cap (Bellco, N.J.) and placed on a gyratory shaker at 120 rpm at 24°±1° C. in darkness. Suspension cultures were formed in approximately 3 to 10 days. Initially, medium was exchanged by suction filtering the flask contents through a buchner funnel containing a miracloth filter (Calbiochem), and resuspending all the biomass in fresh medium. Upon cell growth, 1-2 g (fresh weight) of cells were generally transferred into a new 125 ml flask containing 25 mL of fresh medium and were thereafter subcultured weekly.

Example 4

Growth of Suspended Cells

The typical growth rates and cell densities achieved in suspension cultures of representative species are listed in Table 4.

As a detailed example, the increase in biomass (fresh and dry weight) with time for *Taxus chinensis* line K-1 is shown in FIG. 1. The maximum growth rate was measured by taking the slope at points of most rapid biomass increase on the growth curves. Cell cultures of *Taxus chinensis* grew at a maximum doubling time of 2.5 days. This growth rate is significantly higher than that reported previously for *Taxus* species suspension cultures. For example, Christen et al. (1991) reported a 5- to 10-fold increase in biomass after 3 to 4 weeks of culture, which translates to an average doubling time for *Taxus brevifolia* suspensions of 7 to 12 days.

The ability to cultivate cells at a high density is important in maximizing the volumetric productivity of a cell culture process. Whereas cultures of *Taxus brevifolia* reached a cell density of less than 1 g dry weight per liter (calculated from data presented in Christen et al. (1991)), suspensions of *Taxus chinensis* were able to reach densities of up to 8 to 20 g dry weight per liter after 18 days of growth. The viability of cells was determined by staining cells with a 0.05% solution of fluorescein diacetate in acetone (Widholm, 1972), and by counting the number of green fluorescing cells upon excitation with blue light in an inverted fluorescence microscope (Olympus IMT-2, Japan). Cell viability was higher than 90% throughout the growth phase.

The ability to cultivate cells under rapid growth conditions to high cell densities while retaining high viability is an important pre-requisite to the economic operation of a plant cell culture process for producing taxol and taxol-like compounds.

Example 5

Analysis of Taxol and Taxanes

5.1. ELISA Methods

ELISA analysis for taxol (Hawaii Biotech) was used for large scale screening of cell lines, This method provides high sensitivity (0.1 ng/mL), however, because a polyclonal antibody is used, cross-reactivity with other taxanes is observed. Preparative (analytical scale) HPLC with fraction collection showed cross-reactivity with 10-deacetyltaxol, 7 xylosyl- 10-deacetyltaxol, cephalomannine, 10-deacetyl-7epitaxol, 7 epitaxol, as well as other unidentified taxanes. Despite such cross-reactivity this method was found to be extremely useful for detection of taxane production and allowed large numbers of cell lines to be screened quickly. Cell extracts showing significant production of taxanes were then analyzed in detail using the HPLC procedure outlined below.

5.2. Extraction of Taxol and Related Taxanes

Extraction of taxanes from supernatants were performed by two methods, depending on the concentrations present in the media. When sufficient amounts of taxanes are present in liquid media, samples were prepared very rapidly and efficiently. Media (2 mL) were dried completely (in vacuo) and a measured amount of methanol (0.5–2.0 mL) was added. This mixture was agitated ultrasonically until complete dissolution or dispersion of the sample was accomplished. Solids were removed by centrifugation prior to HPLC analysis. Quantitative recoveries have been obtained at 1 mg/L levels with detection levels well below 0.1 mg/L.

When concentration of taxanes in the culture supernatants were low, the medium was extracted three times with an equal volume of a mixture of methylene chloride and isopropyl alcohol (IPA) (9:1 by vol.). The organic layer was reduced to dryness and reconstituted in a measured volume of methanol (50–250 mL). Multiple extraction typically recovered 90–95% of the taxol, cephalomannine, and baccatin III at 0.6 mg/L levels.

Cell materials were extracted by freezing freshly harvested cells ($-5°$ C.), followed by vacuum drying, and methanol soxhleting for 50 cycles. 70 to 80% of the taxanes were generally recovered with 10–15% measurable decomposition. The extraction of solid media and callus was accomplished identically to that of cells, however, methylene chloride/IPA vs. water partitioning of the final methanol extract was always performed.

5.3. High Performance Liquid Chromatography Methods

Analytical high performance liquid chromatography (HPLC) was performed on a high-carbon loaded diphenyl column (Supelco, 5 mM, 4.6 mm X 25 cm) with an LDC Analytical binary gradient high pressure mixing system consisting of CM3500/CM3200 pumps, a CM4100 variable volume autosampler and an SM5000 photo diode array detector interfaced to a Total Peripherals 486 personal computer. Column temperature was regulated at 35° C. with an Eldex CH150 column oven. Quantitative HPLC analysis of taxanes was accomplished using a binary gradient elution scheme as follows:

| Time | % Eluant A | % Eluant B | Flow |
|------|-----------|-----------|---------|
| 0 | 75 | 25 | 1 mL/min |
| 40 | 35 | 65 | " |
| 42 | 25 | 75 | " |
| 47 | 25 | 75 | " |
| 50 | 75 | 25 | " |

Eluant A = 0.015 mM $KH_2PO_4$ brought to pH 3.5 with trifluoroacetic acid
Eluant B = acetonitrile The chromatographic methods used resemble several published methods (Witherup et al. 1989) with the exceptions that a phosphate buffer containing trifluoroacetic acid has been used and that a longer gradient is employed. These differences significantly improve the resolution of taxol and other taxanes from the mixture. The relative retention times observed for taxanes are shown below. Taxol elutes between 31 and 33 minutes depending on the column and hardware used.

| Compound | Relative Retention Time |
|----------|------------------------|
| 10-deacetylbaccatin III | 0.38 |
| baccatin III | 0.56 |
| 7-xylosyl-10-deacetyltaxol C | 0.80 |
| 10-deacetyltaxol C | 0.87 |
| cephalomannine | 0.94 |
| 10-deacetyl-7-epitaxol C | 0.98 |
| taxol C | 1.00 |
| 7-epitaxol | 1.12 |

The retention times of taxol, cephalomannine and baccatin III were determined using authentic samples obtained from the National Cancer Institute. The retention times of the other taxanes listed above were compared to analytical standards provided by Hauser Chemical (Boulder Colo.). Identification of known taxanes was based on retention time and ultraviolet spectral comparisons. Quantitation of taxol, cephalomannine and baccatin III was based on response factors determined from authentic materials. Quantitation of 10-deacetylbaccatin III was performed using the response factor determined for baccatin III. Quantitation of the remaining taxol derivatives was based conservatively on the response factor measured for taxol.

Each of the standards (10 mL) was typically injected (initially then after 3 or 4 samples) and areas for each of the three components were integrated. Response factors for each of the components was obtained by linear least-squares analysis of the data. 10 mL of each sample was injected and the amount per injection was calculated based on the standard data regression. These results were converted to amount per liter or percent dry weight. FIG. 4 illustrates a typical chromatogram of a supernatant sample.

5.4. MS/MS Confirmation of Taxol

The identity of taxol in cell culture supernatant has been confirmed using an MS/MS method (as shown in FIG. 6) which couples flow injection with ion spray atmospheric pressure chemical ionization. Details of the procedures used for acquiring the data presented in FIG. 6 were as follows: Mass Spectrometer: Sciex API 3 triple quadrupole with an atmospheric pressure ionization source. Nitrogen was used as the curtain gas and argon was used as the collision gas for the CID spectra. Interface: Ion Spray interface producing ions by Ion Evaporation Ionization (Electrospray). Zero air was used as the nebulizer gas. LC Pump: ABI 140B dual syringe pump operating at 5 μL/minute. Solvents: 50/50 acetonitrile/H20 2mM NH4OAc+0.1% formic acid. Injection Volume: 5 μL, all spectra taken by flow injection analysis. This method provided unequivocal confirmation for the presence of taxol in cell culture samples, and also provided quantitation with excellent agreement to HPLC results.

Example 6

Taxol production by various species

The taxol produced by cell cultures of various *Taxus* species is summarized in Table 5. Callus was cultivated for 20 days in the dark on the indicated solidified medium for each species. The cells and medium were dried and methanol-extracted together, and assayed by either ELISA or HPLC as indicated. The results obtained with *Taxus chinensis* cultures are elaborated further in Examples 7 and 8.

Example 7

7.1 Production in growth medium

The production of taxol and related taxanes commenced within the first 2 days of transfer into growth Medium A. The maximum taxol observed was on day 15, at 8.81 μg/flask, which corresponds to 0.44 mg/liter taxol. Of this, 46.1% was present in the extracellular medium. On day 15, the total taxane concentration was 72.87μg/flask, or 3.6 mg/liter, of which 58.6% was present in the extracellular medium. The viability of cells was always greater than 90% as measured by fluorescence staining (Example 4), suggesting that the presence of extracellular taxol and taxanes was due to secretion rather than due to cell lysis. The ability of cells to secret taxol and taxanes will be an important aspect of continuous operation.

7.2 Medium exchange for productivity enhancement

Figure 2A:
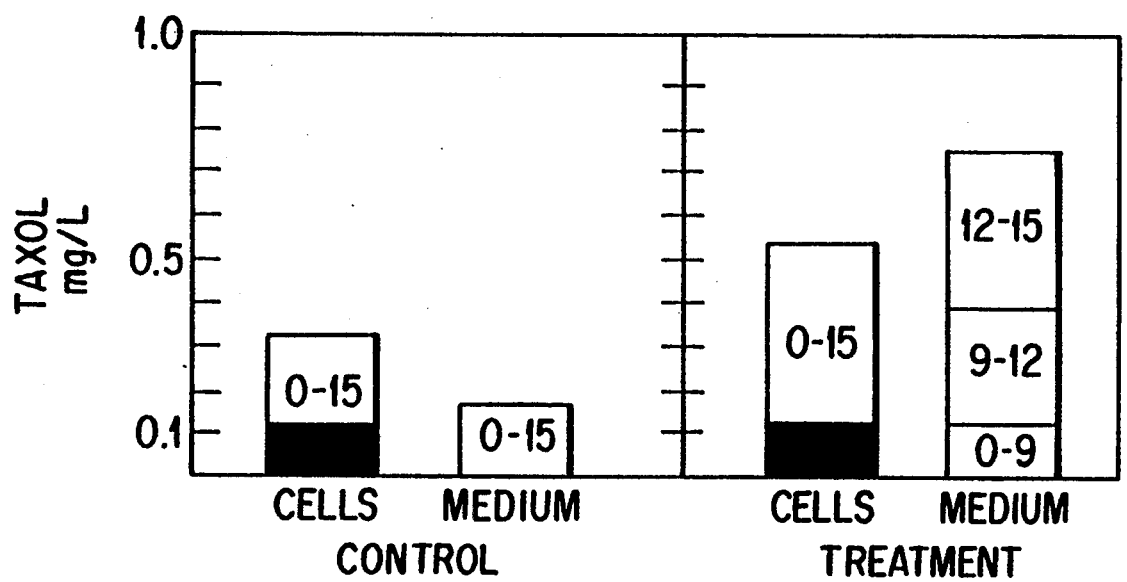
FIG. 2. Effect of medium exchange on days 9 & 12 on taxol (A) and total taxane (B) productivity in a 15-day experiment. The numbers in each box represent the time interval (days) over which the product was produced. The darkened portion of the intracellular boxes represents the taxol or total taxanes that were present in the cell inoculum at the start of the experiment. All treatments were performed in duplicate. *Taxus chinensis* suspension cell line K-1 was used with Medium A as elaborated in Table 2.
Figure 2B:
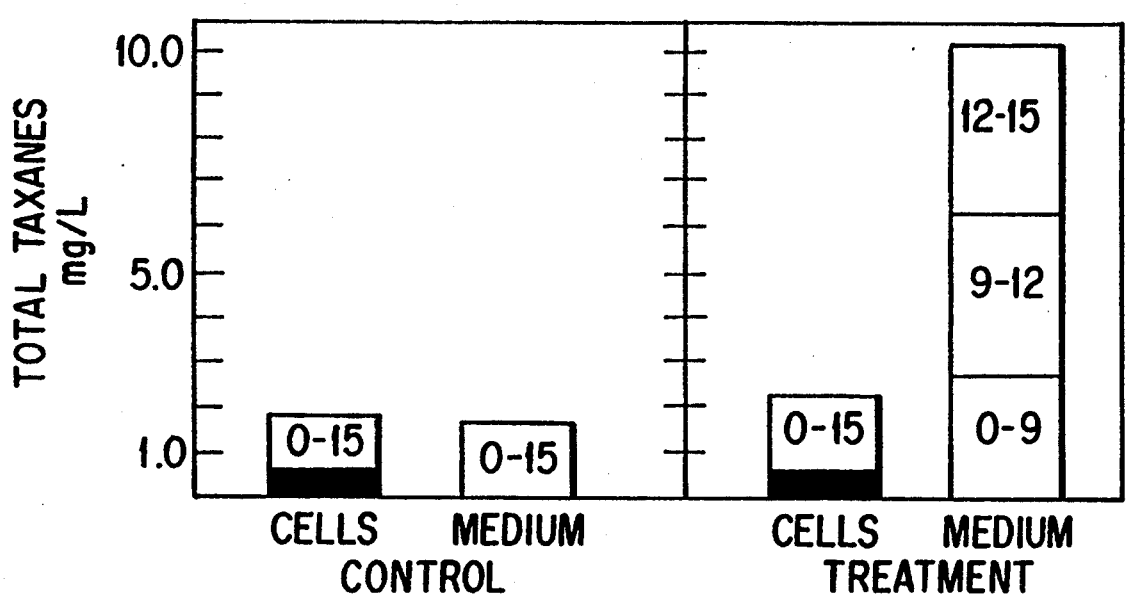

Significant improvements in taxol and total taxane productivity were obtained by aseptically suctioning off growth Medium A on day 9, replacing with fresh medium and repeating the procedure on day 12. The experiment was terminated on day 15, and the results are shown in FIG. 2. The important increases in productivity due to medium exchange are summarized in Table 6. The total amounts of taxol and taxanes produced were ca. 4.6-fold higher with medium exchange compared to controls without treatment. Importantly, ca. 4.9-fold higher taxol, and ca. 5.9-fold higher total taxanes were recovered in the extracellular medium compared to controls without medium exchange treatment.

The ability to markedly enhance taxol and total taxane productivities, and moreover, to cause extracellular product accumulation is important for operation of an efficient, continuous process with biomass reuse and simplified downstream purification.

7.3. Effect of Light on taxane production in growth medium

Light is known to play an important role not only in photosynthesis, but also in various aspects of secondary metabolism in plant cell cultures (Seibert and Kadkade 1980). Whereas the experiments described in Examples 4, 7.1, and 7.2 were conducted in darkness, the response of *Taxus chinensis* cultures to light is described here.

Figure 3:
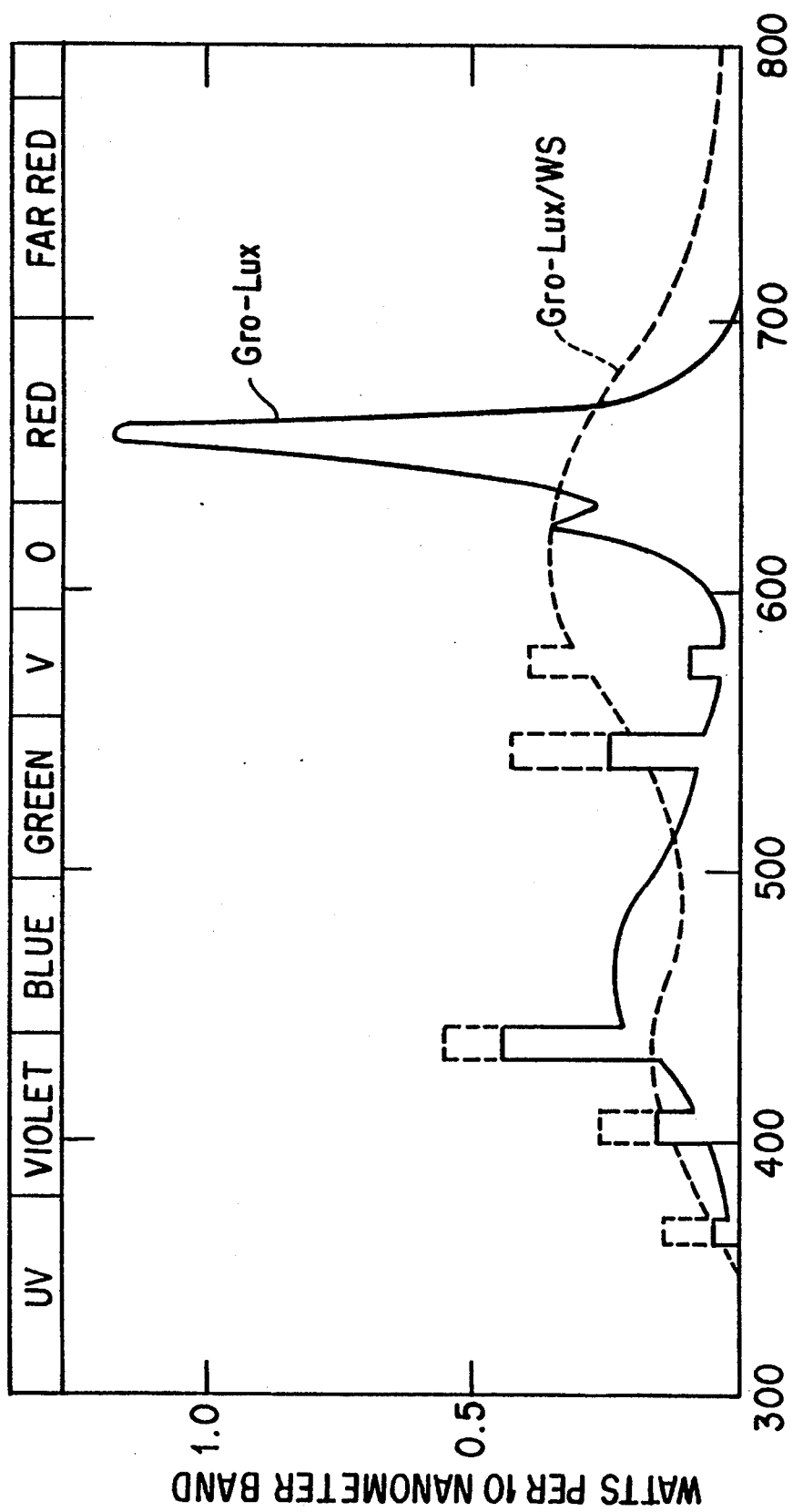
FIG. 3. Spectral characteristics of a Standard Gro-Lux lamp (GTE Sylvania, Danvers, Mass.) used in Example 7.3.
Figure 4A:
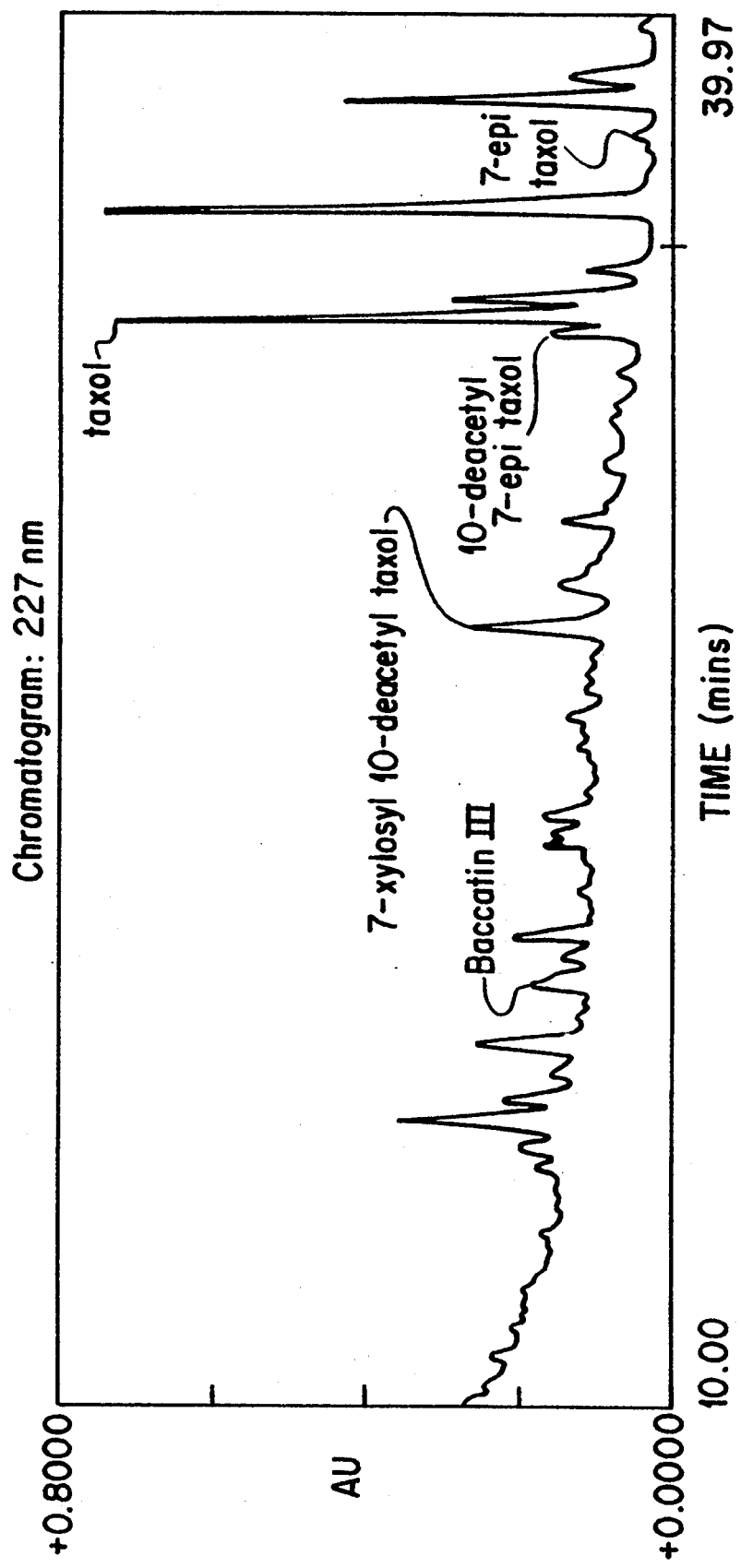
FIG. 4. Taxane production in *Taxus chinensis* cell suspension K-1. The portion of the chromatogram from 10 to 40 minutes is shown. Diode array scans of selected taxane peaks show a characteristic taxane UV absorption spectrum, with a peak at 227 nm.
Figure 4B:
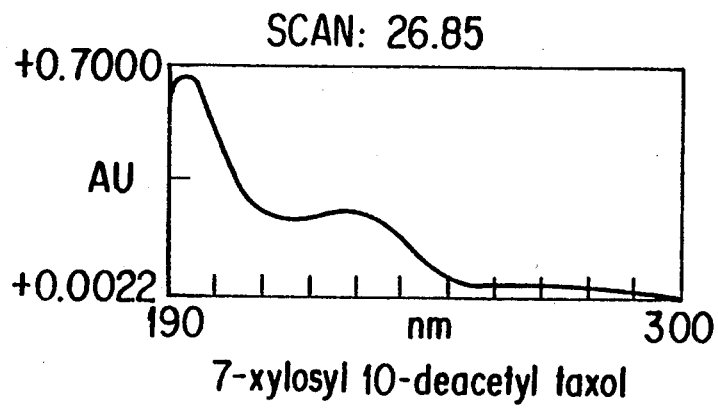
Figure 4C:
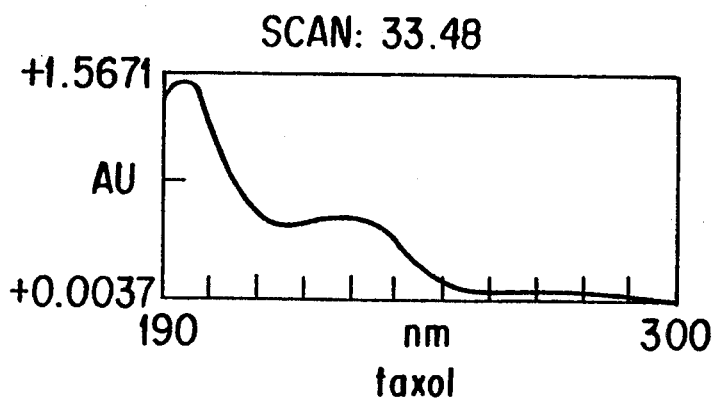
Figure 4D:
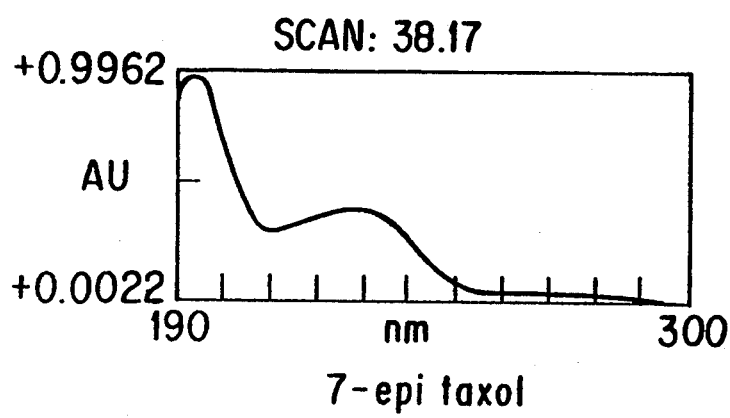

One gram fresh weight of 7-day old cells of *Taxus chinensis* line K-1 were inoculated in 25 ml of growth Medium A (see Table 2) in 125 ml Erlenmeyer flasks and incubated at 24°±1° C. on a gyratory shaker at 120 rpm. Duplicate flasks were placed in the dark and under a Standard GroLux lamp at a distance of 3 feet. Spectral characteristics of the lamp are shown in FIG. 3. Results are shown in Table 7.

Exposure of cultures to light did not affect total taxane levels or the extent of extracellular accumulation. However, taxane profiles were significantly altered in the two treatments. For example, cells cultivated in the light produced 2.8 fold higher taxol than did cells in the dark. The proportion of extracellular taxol was also significantly higher than in the dark treatment (76% vs 56%). The use of light treatment, especially of specific spectral quality, would thus be extremely useful in a cell culture process for taxol production.

Example 8

Elicitors

The term elicitors is used for compounds of biological (or biotic) and non-biological (or abiotic) origin that cause an increase in secondary metabolism when added to plant cell cultures.

While a number of elicitors have been found useful, a representative illustrative example is described here in detail, namely, the use of chitosan glutamate. While chitosan has been previously tried as an elicitor in some plant cell culture systems, the accompanying toxic reactions such as browning and loss of viability have made its use impractical (Beaumont and Knorr 1987). Indeed such toxic side reactions are a common drawback of many elicitors reported in the literature. The use of chemically modified chitosans such as chitosan glutamate to specifically induce taxol and taxane biosynthesis while circumventing toxic side-effects is a novel approach.

Suspensions of *Taxus chinensis* line K-1 grown in Medium D for 7 to 8 days were suction filtered aseptically using a sterile Buchner funnel fitted with a miracloth (Calbiochem) filter. 2 g fresh weight cells were aseptically transferred to 25 ml of medium C (see Table 2) in a 125-mL Erlenmeyer flask. A solution of 0.05% chitosan glutamate was prepared freshly and filter-sterilized through a 0.22 micron cartridge filter. 825 μL of this solution was added to the flask at the start of the experiment, corresponding to a level of 165 mg elicitor per gram dry weight cells. The flasks were incubated at 24°±1° C. on a gyratory shaker at 110 rpm in the dark. The flasks were destructively sampled on day 15, and observations on growth, color of the cells and medium and cell viability were recorded. Freeze-dried samples were methanol-extracted for taxol and taxanes as described in Example 5, and were analyzed by HPLC. The results of this experiment are shown in Table 8.

Elicitor treatment resulted in a modest improvement in the per-cell total taxane production (0.53% vs. 0.42% dry weight taxanes) over non-treated controls. The non-toxic nature of the elicitor is evident from the high viabilities (75–80%) observed in both treatments. In fact, an increased dry weight in elicitor treatment compared to controls has been reproducibly observed (14.2 g/l vs. 10.1 g/l dry weight). The higher cell densities resulted in an 1.8-fold greater titer of total taxanes in the elicitor treatment, i.e., 75.8 mg/L versus 42.4 mg/L for the control.

The elicitor treatment resulted in increased taxol biosynthesis, both on a per-cell basis (0.098% vs. 0.054% dry weight taxol, a 1.8-fold increase) and in a titer comparison (13.9 mg/L versus 5.4 mg/L, a 2.6-fold increase). The extent of secretion was higher for the elicitor treatment compared to the control (85% versus 72% extracellular product).

The elicitor treatment described herein results in increased taxol production, a more favorable product profile, enhanced product secretion and retention of high cell viability. These production characteristics represent a significant improvement for a cell culture process for taxol production.

Example 9

Production Medium Development

In an effort to increase taxol productivities over the levels described in example 6, nutrient levels were manipulated to formulate special 'production media'. 7 to 8 day old suspensions of *Taxus chinensis* line K-1 grown in Medium D were suction filtered aseptically using a sterile Buchner funnel fitted with a miracloth (Calbiochem) filter. 500 mg fresh weight cells were aseptically transferred to 5 ml of production Media B and C (see Table 2). The vessels were incubated for varying time periods of 18, 25, and 42 days at 24°±1° C. on a gyratory shaker at 110 rpm in the dark. Treatments were destructively sampled, and observations on growth, color of the cells and medium, and cell viability were recorded. Freeze-dried samples were methanol-extracted for taxol and taxanes as described in Example 5, and were analyzed by HPLC.

9.1. Results of 18-Day Cultivation

*Taxus chinensis* cell cultures responded to the altered medium compositions by producing significant levels of taxanes and taxol. These data are summarized in Table 9, and a sample chromatogram is shown in FIG. 4. In medium B, 99.8 mg/liter of total taxanes were produced, with 24.1 mg/liter of pure taxol. In Medium C, 110 mg/liter of total taxanes were produced, with 21.3 mg/liter of taxol. On a dry weight basis, cells produced 0.18% dry weight taxol on medium B, and 0.065% dry weight taxol on medium C.

9.2. Prolonged Cultivation

Figure 5B:
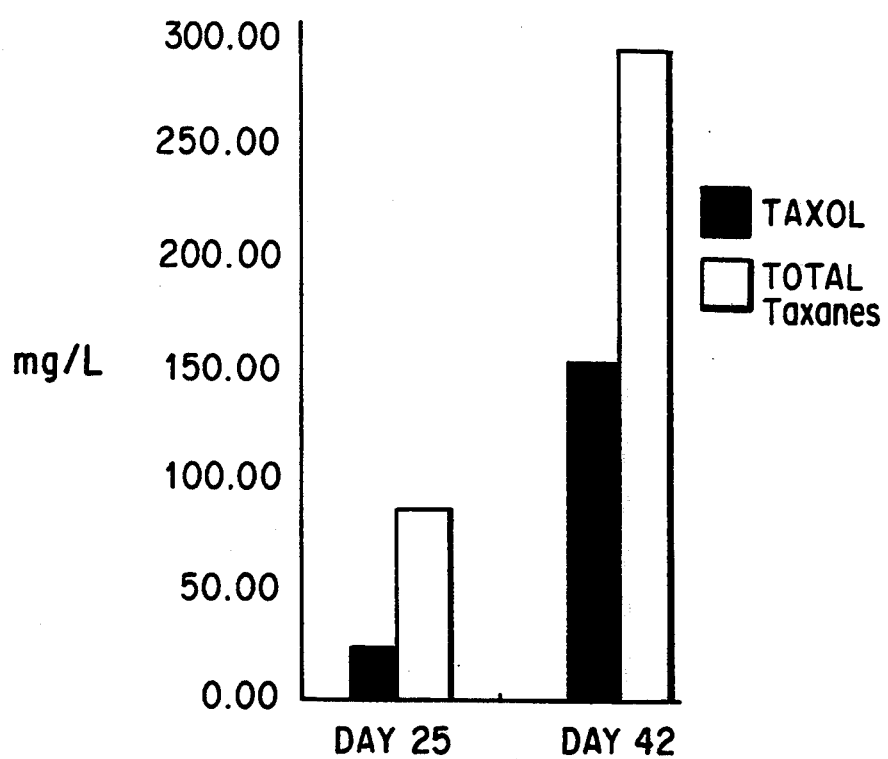
FIG. 5. Taxol and taxane production after prolonged cultivation in Medium C by *Taxus chinensis* cell line K-1. The upper panel tabulates the data for the known and unknown taxanes, whereas the lower panel shows incremental taxol and taxane production in the 25 to 42 day time period.
Figure 6A:
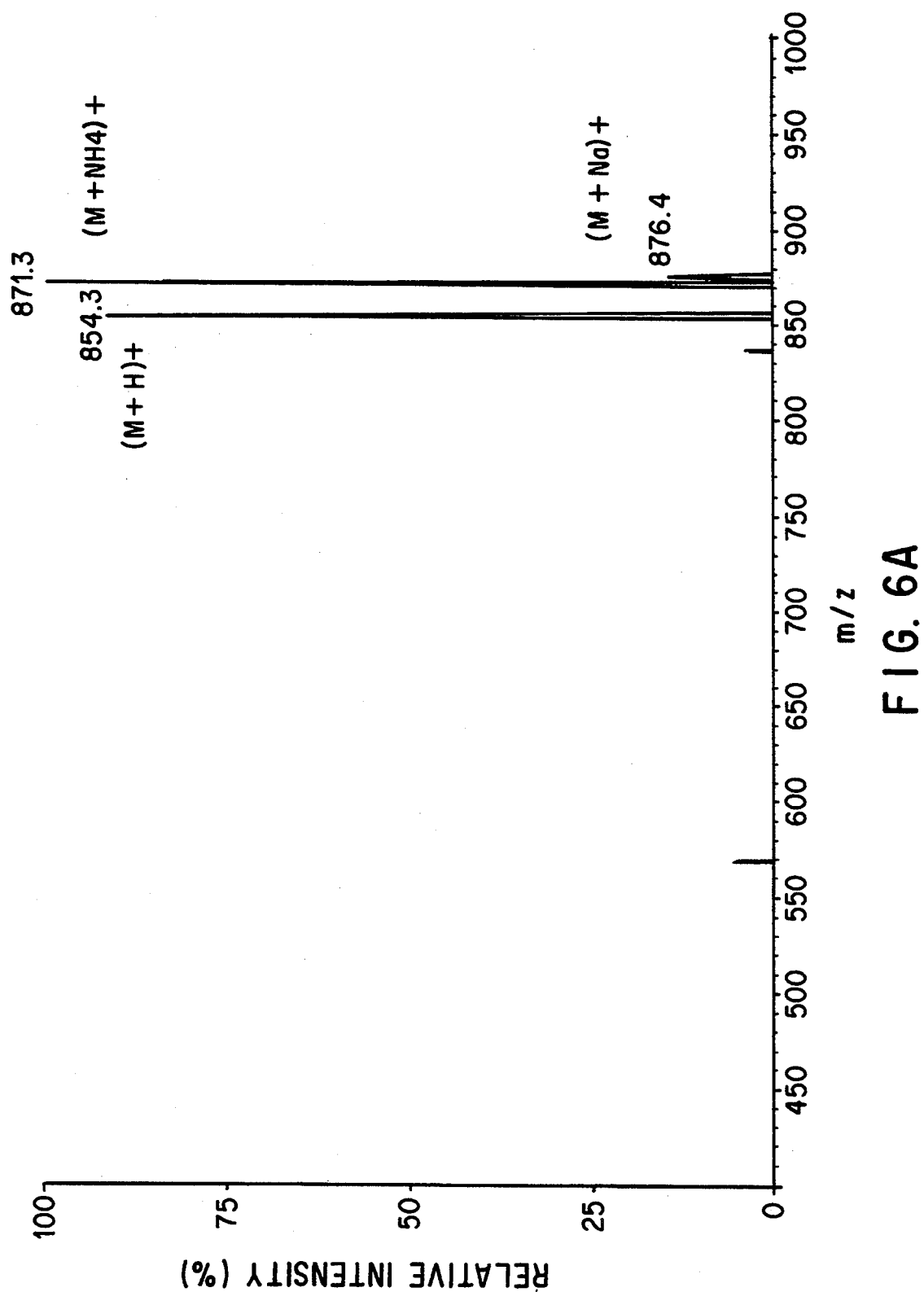
FIGS. 6A, 6B, 6C, and 6C. MS/MS confirmation of taxol in cell culture supernatant. Panel
Figure 6B:
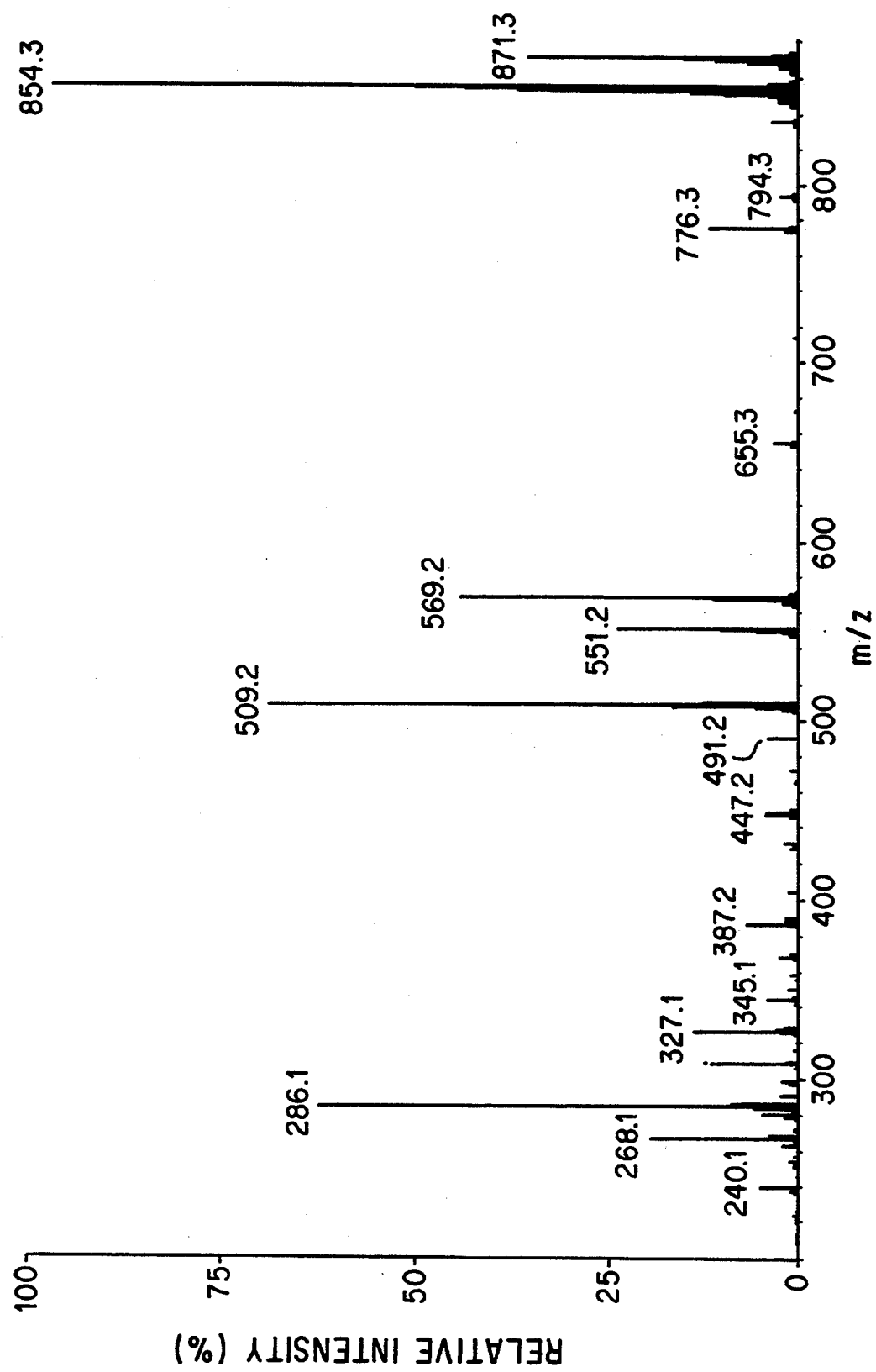
Figure 6C:
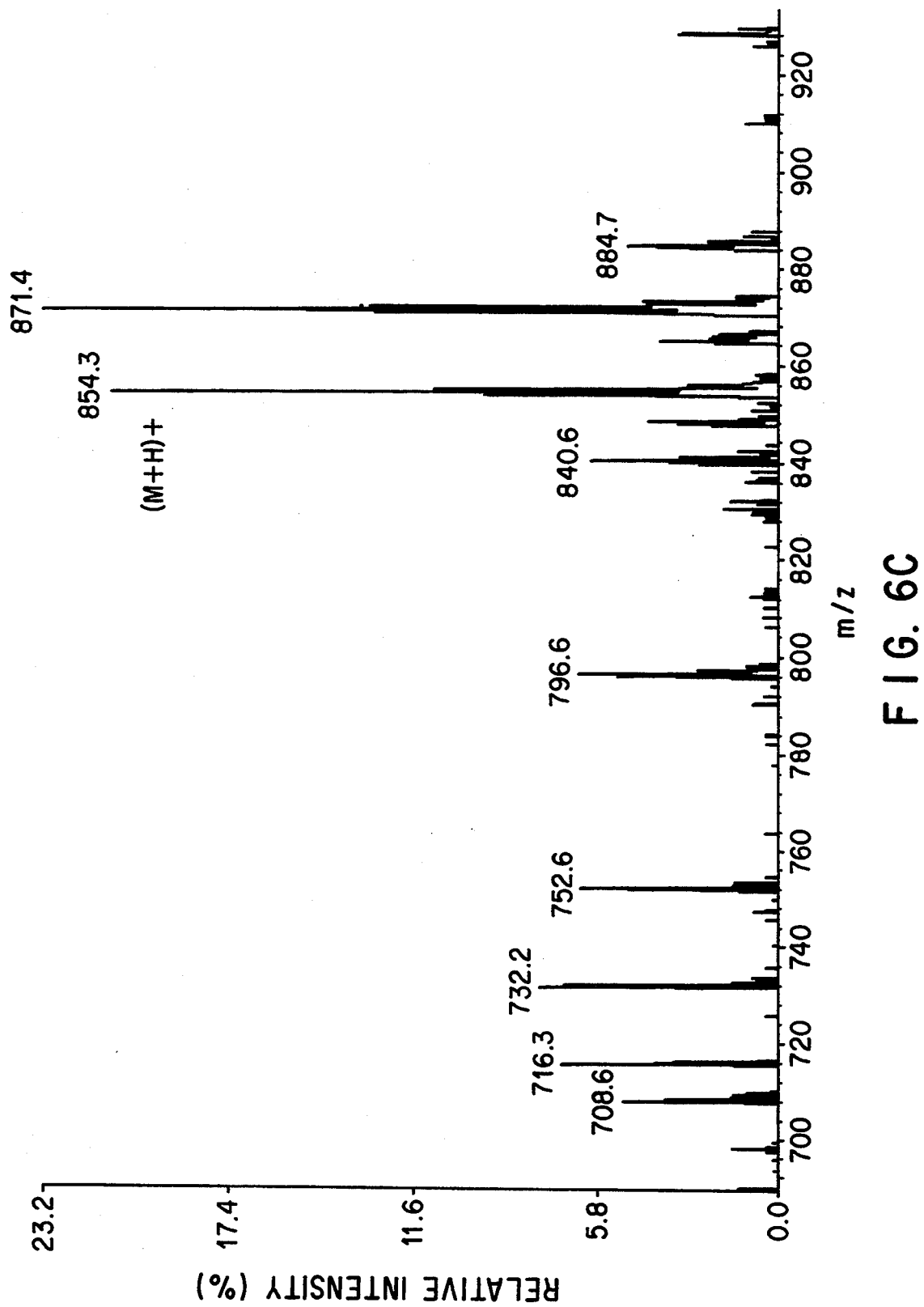
Figure 6D:
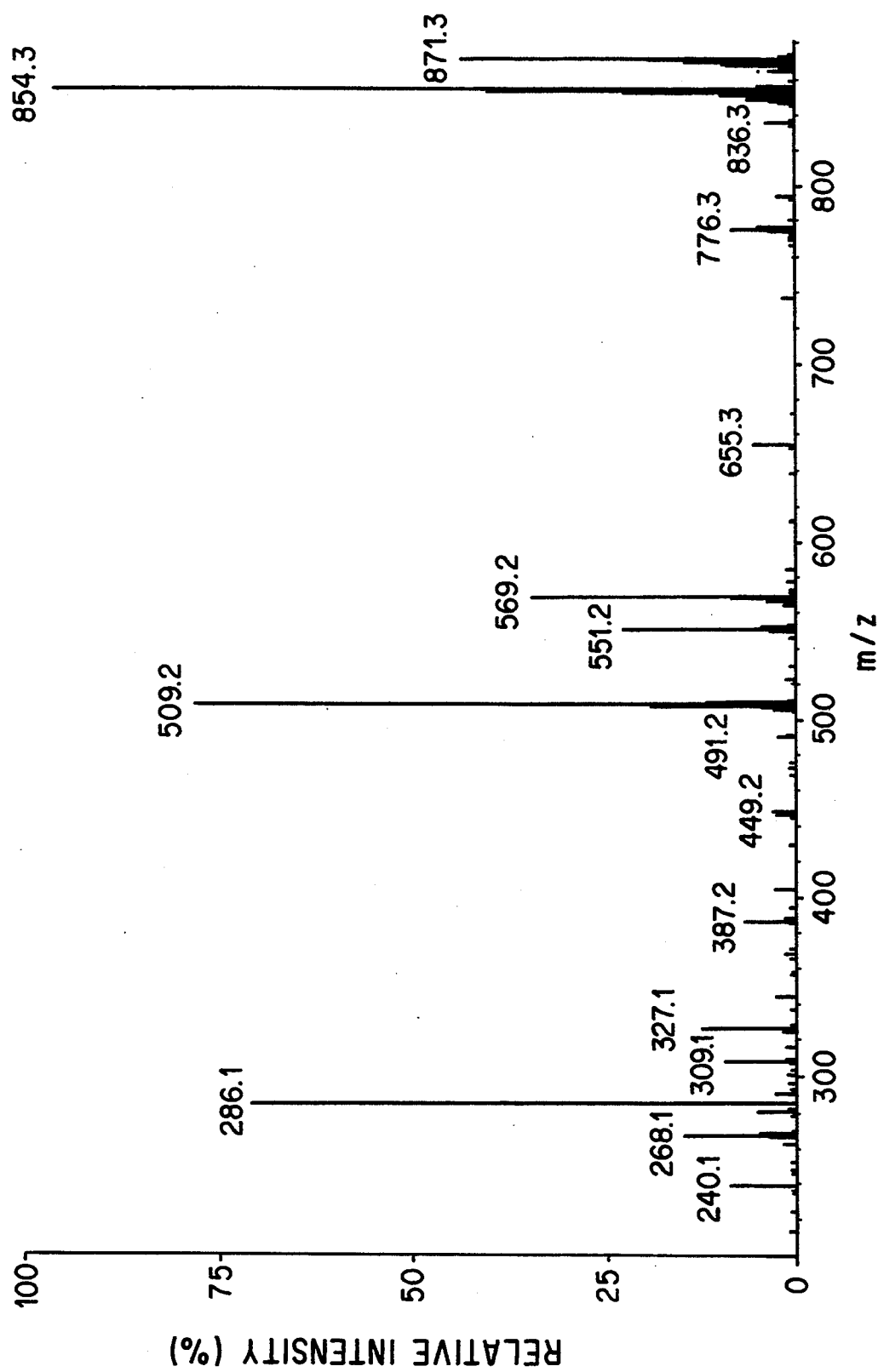
FIG. 6D shows the corresponding daughter spectrum of m/z 871 and provides unequivocal evidence for the presence of taxol in cell culture supernatant.

Taxol and taxane production after prolonged cultivation of *Taxus chinensis* cells (line K-1) for 25 and 42 days was studied in medium C, the results for which are summarized in FIG. 5. The following significant observations can be summarized:

(i) *Taxus* suspension cultures are capable of producing significant levels of taxol and other taxanes. Highest accumulation occurred at 42 days, with 0.32% dry weight taxol, and 0.62% dry weight total taxanes; corresponding to titers of 153 mg/L taxol and 295 mg/L total taxanes based on final medium volume. The analysis of this sample by tandem mass spectrometry confirmed the presence of taxol as shown in FIG. 6. Quantitation by MS/MS showed excellent agreement with HPLC.

(ii) The rate of taxol biosynthesis between days 25 and 42 was at ca. 7.6 mg taxol per liter per day assuming linear production in the 17-day period. This rate is significantly higher than the rate of production in the first 25 days. The rate of total taxane biosynthesis between days 25 and 42 was 12.3 mg per liter per day.

(iii) Production medium formulations can induce up to 45-fold increases in specific taxol content compared to rapid growth conditions such as those described in Example 7

(iv) The product spectrum can be manipulated so as to funnel biosynthesis towards the desired end-product taxol, while minimizing production of undesirable taxanes. For example, on day 25, taxol constituted 28% of the total taxanes and on day 42, taxol constituted 52% of the total taxanes in contrast to growth medium (see Example 7.1), in which taxol constituted only 12.2% of the total taxanes. This ability to manipulate product profiles will have important repercussions for downstream purification and for product purity-related regulatory issues. For example, the ability to suppress production of the taxane by-product, cephalomannine could greatly simplify downstream purification compared to purification of taxol from bark tissue.

(v) *Taxus* cell cultures have been induced to secrete significant amounts of taxol (87% on day 42) and other taxanes. That the presence of extracellular taxol and taxanes is due to secretion rather than due to cell lysis is corroborated by several independent observations: (a) continued biosynthesis occurred between days 25 and 42, suggesting that cells were viable and active. Independent observations have shown that >70% viability have been observed after 18 days in production medium, (b) different percentages of different taxanes were secreted. If cells had lysed, the percentage in the medium might have been expected to be similar for the different taxanes.

(vi) The ability of this *Taxus* cell line to thrive and produce taxol at high rates in an extracellular environment so rich in product is particularly worth noting.

(vii) The *Taxus* cell line with which these results were obtained is also capable of rapid growth to high cell densities, and expressed the reported productivities after 20 generations under rapid-growth conditions, attesting to its stability and commercial potential.

The levels of taxol and taxanes produced by cell lines of *Taxus chinensis* under the conditions described herein are higher than previously reported results by a factor of 35- to 150-fold. For example, Christen et al. (1991) reported the production of 1 to 3 mg/liter of taxol by suspension cultures of *Taxus brevifolia* after 2 to 4 weeks of cultivation. Wickeramesinhe and Arteca (1991) reported the production of taxol at 0.009% dry weight in cell cultures of *Taxus media*.

In summary, our data show that with careful initiation and selection of *Taxus chinensis* cultures, and with specially formulated growth medium conditions, cells can be induced to grow rapidly to high cell densities. When these cells are transferred to production medium conditions, cells are able to biosynthesize and secrete significant levels of taxol and other taxanes for prolonged periods while maintaining high viabilities. The incorporation of periodic medium exchange, light and elicitors with production medium results in further synergistic productivity enhancements. These properties are critical prerequisites for an efficient commercial process for taxol and taxane production using tissue culture technology.

REFERENCES

M. Asada and M. L. Shuler. 1989. Stimulation of Ajmalicine Production and Excretion from Catharanthus roseus: Effects of adsorption in situ, Elicitors, and Alginate Immobilization. *Appl. Microbiol. Biotechnol.*, 30, 475–481.

M. D. Beaumont and D. Knorr. 1987. Effects of immobilizing agents and Procedures on Viability of Cultured Celery (*Apium graveolens*) Cells. *Biotechnol. Lett.* 9, 377-382.

J. Berlin and L. Witte. 1988. Formation of Mono- and Diterpenoids by Cultured Cells of Thuja Occidentalis. *Phytochemistry.* 27, 127-132.

C. H. Bornman. 1983. Possibilities and Constraints in the Regeneration of Trees from Cotyledonary needles of *Picea abies* in vitro. *Physiol. Plant.* 57, 5-16.

A. A. Christen, D. M. Gibson and J. Bland. 1991. Production of Taxol or Taxol-Like Compounds in Cell Culture. U.S. Pat. No. 5,019,504.

A. G. Darvill and P. Albersheim. 1984. Phytoalexins and their Elicitors-A Defense Against Microbial Infection in Plants. *Ann. Rev. Plant Physiol.* 35, 243-275.

N. E. Delfel and J. A. Rothfus. 1977. Antitumor Alkaloids in Callus Cultures of *Cephalotaxus harringtonia*. Phytochemistry. 16, 1595-1598.

J. N. Denis, A. Correa and A. E. Greene. 1991. Direct Highly Efficient Synthesis from S-Dextro Phenylglycine of the Taxol and Taxotere Side Chains. *J. Org. Chem.*, 56, 6939-6942.

J. Denis, A. E. Greene, D. Guenard and F. Gueritte-Voegelein. 1990. Process for Preparing Taxol. U.S. Pat. No. 4,924,011.

J. N. Denis, A. E. Greene, D. Guenard, F. Gueritte-Voegelein, L. Mangatal and P. Potier. 1988. Highly Efficient Practical Approach to Natural Taxol. *J. Am. Chem. Soc.*, 110, 5917-5919.

J. Ebel. 1984. Induction of Phytoalexin Synthesis in Plants Following Microbial Infection or Treatment with Elicitors. *Bioregulators: Chemistry and Uses.* 257-271.

U. Eilert. 1987. Elicitation: Methodology and Aspects of Application. In "Cell Culture and Somatic Genetics of Plants," Vol. 4, F. Constabel and I.K. Vasil (eds.) Academic Press, New York, pp. 153-196.

P. F. Heinstein. 1985. Future Approaches to the Formation of Secondary Natural Products in Plant Cell Suspension Cultures. *Journal of Natural Products.* 48, 1-9.

R. A. Holton. 1991. Method for Preparation of Taxol Using an Oxazinone. U.S. Pat. No. 5,015,744.

M. Jaziri, B. M. Diallo, M. H. Vanhaelen, R. J. Vanhaelen-Fastre, A. Zhiri, A. G. Becu and J. Homes. 1991. Enzyme-linked Immunosorbent Assay for the Detection and the Semi-Quantitative Determination of Taxane Diterpenoids Related to Taxol in *Taxus* sp. and Tissue Cultures. *J. Pharm. Belg.*, 46, 93-99.

H. Miyasaka, M. Nasu, T. Yamamoto, Y. Endo and K. Yoneda. 1986. Regulation of Ferruginol and Cryntotanshinone Biosynthesis in Cell Suspension Cultures of *Salvia Miltiorrhiza*. Phytochemistry. 25, 637-640.

G. F. Payne, V. Bringi, C. Prince and M. L. Shuler. 1991. Plant Cell and Tissue Culture in Liquid Systems, Hanser Publishers, Munich.

R. J. Robins and M. J. C. Rhodes. 1986. The Stimulation of Anthraquinone Production by *Cinchona ledgeriana* Cultures with Polymeric Adsorbents. *Appl. Microbiol. Biotechnol.*, 24, 35-41.

E. K. Rowinsky, L. A. Cazenave and R. C. Donehower. 1990. Taxol: A Novel Investigational Antimicrotubule Agent. *J. Natl. Cancer Inst.*, 82, 1247-1259.

M. Seibert and P. G. Kadkade. 1980. Light. In Plant Tissue Culture as a Source of Biochemicals. E. J. Staba (ed), CRC Press, Boca Raton, Florida, pp. 123-141.

W. van Uden, N. Pras and T. M. Malingre. 1990. The Accumulation of Podophyllotoxin,B-D-glycoside by Cell Suspension Cultures Derived from the Conifer *Callitris drummondii*. *Plant Cell Reports.* 9, 257-260.

M. C. Wani, H. L. Taylor, M. E. Wall, P. Coggon and M. T. McPhail. 1971. Plant Antitumor Agents. VI. Isolation and Structure of Taxol, a Novel Antileukemic and Antitumor Agent from *Taxus brevifolia*. J. Am. Chem. Soc., 93, 2325-2327.

P. J. Westgate, A. H. Emery, P. M. Hasegawa and P. F. Heinstein. 1991. Growth of *Cephalotaxus harringtonia* Plant Cell Cultures. *Appl. Microbial Biotechnol.* 34, 798-803.

E. R. M. Wickeramesinhe and R. N. Arteca. 1991. Habituated Callus Cultures of *Taxus media* cultivar Hicksii as a Source of Taxol (Abstract). *Plant Physiol.*, 96, (Supplement) p. 97.

J. M. Widholm. 1972. The Use of Fluorescein Diacetate and Phenosafranine for Determining Viability of Cultured Plant Cells. *Stain Technol.*, 47, 189-194.

K. M. Witherup, S. A. Look, M. W. Stasko, T. G. McCloud, H. J. Issaq and G. M. Muschik. 1989. HPLC Separation of Taxol and Related Compounds from *Taxus brevifolia*. *J. Liq. Chrom.*, 12, 2117-2132.

K. M. Witherup, S. A. Look, M. W. Stasko, T. J. Ghiorzi, G. M. Muschik. 1990. *Taxus* spp. Needles Contain Amounts of Taxol Comparable to the Bark of *Taxus brevifolia*: Analysis and Isolation. *Journal of Natural Products.* 53, 1249-1255.

L. X. Xu and A. R. Liu. 1991. Determination of Taxol in *Taxus chinensis* by HPLC Method. *Acta Pharmeceutica Sinica,* 26, 537-540.

TABLE 1. a.

List of Elicitors Used in Elicitation of *Taxus* spp. Cell Cultures

I. Biotic Elicitors (microorganisms)

*Botrytis cinerea*
*Phytophthora megasperma*
*Pinellas stripticum*
*Oligosporus* sp.
*Pythium mamiallatum*
*Pythium sylvaticum*
*Verticillium dahliae*
*Verticillium* sp.
*Penicillium minioluteum*
*Phytophthora lateralis*
*Cytospora cincta*
*Cytospora leucostoma*
*Alternaria brassicicola*
*Alternaria solani*
*Alternaria cucumerina*
*Botrytis squamosa*
*Cochliobolus heterostrophus*
*Colletotrichum trifolii*
*Colletotrichum orbiculum*
*Colletotrichum graminicola*
*Colletotrichum gloeosporioides*
*Cylindrocladium floridanum*
*Fusarium crookwellense*
*Fusarium heterosporium*
*Fusarium oxysporum* f. sp. *conglutinans*
*Fusarium oxysporum* f. sp. *lycopersici*
*Fusarium oxysporum* f. sp. *pisi*
*Gibberella zeae*
*Gaeumannomyces graminis* var. *tritici*
*Geotrichum* sp.
*Leptosphaeria torrae*
*Nectria haematococca* MPVI
*Mycosphaerella pinodes*
*Ophiostoma ulmi*
*Phoma lingam*
*Phoma pinodella*
*Phytophthora infestans*
*Pythium aristosporum*
*Pythium graminicola*

TABLE 1. a.-continued
List of Elicitors Used in Elicitation of *Taxus* spp. Cell Cultures

*Pythium ultimum*
*Rhizoctonia solani*
*Sclerotinia* sp.
*S. nodorum* D-45
*Trametes versicolor*
*Ustilago maydis*
*Venturia inequalis*

II. Biotic Elicitors (Microbial fractions or products)

Chitosan
Lichenan
Glucomannan
Pleuran
Glucan
Carboxymethylglucan
Hydroxymethylglucan
Sulfoethylglucan
Mannan
Xylan
Mannobiose
Mannotriose
Mannopentaose
Mannotetraose
Cellulysin
Multifect XL
Multifect CL
Resinase
Pulpxyme
SP431
Pectinol
Rapidase
Klerzyme
Chitinase III. Abiotic Elicitors (Chemical Stress Agents as well as some naturally occurring biochemicals)

Arachidonic acid
Elaidic acid
Cyclic AMP
Dibutyrl Cyclic AMP
Methyl Jasmone
Cis-Jasmone
Miconazol
Ferulic acid
AMO-1618
Triton X-100
Benzoic acid
Salicylic acid
Propyl gallate
Sesamol
Chlorocholine chloride
3,4-dichlorophenoxy triethyl-(amine)
Chloroethylphosphonic acid
Diethyldithiocarbamic acid
Nordihydroguairetic acid
Dithiothreitol
Sodium metabisulfite
Potassium metabisulfite
d-amino-DL-Phenylalanine
Vanadyl sulfate
Uniconazol
Paclobutrazol
Spermine
Spermidine
Putrescine
Cadavarine
Protamine Sulfate
SKF-7997
MER 29
Ancymidol
Triadimefon
Phosphon D
Thiourea
Dextran Sulfate
Hydroquinone
Chitosan glutamate
Fenpropemorph
Prochloraz
Naptifine
EDU
HTA
MPTA
Glutathione
EGTA
Gibberellins
Abscisic Acid
1,3-Diphenyl urea
Diazolidenyl urea
Phloroglucinol
Sodium alginate
Carrageenan

TABLE 1. b.
List of Precursors, Inhibitors & Stimulants or Activators Used in Regulation of Biosynthesis of Taxol & Taxanes in T. spp. cell cultures.

| Precursors | Inhibitors | Stimulants or Activators |
|---|---|---|
| Phenylalanine | Chlorocholine chloride | Cyclic AMP |
| Lysine | Uniconazol | Dibutyrl Cyclic AMP |
| Tyrosine | Paclobutrazol | Methyl Jasmone |
| Tryptophane | SKF-7997 | Cis-Jasmone |
| Methionine | MER 29 | Chloroethylphosphonic acid |
| Tyramine | Ancymidol | Spermine |
| Sodium acetate | Triadimefon | Spermidine |
| Potassium acetate | Phosphon D | Putrescine |
| Ammonium acetate | Fenpropemorph | Cadavarine |
| Mevalonic acid | Prochloraz | MPTA |
| Farnesyl acetate | Naptifine | DCPTA |
| Geranyl acetate | Miconazol | DIPTA |
| Geranylgeraniol acetate | Silver Nitrate | ACC |
| Tryptamine | Norbornadiene | HTA |
| Menthol | AMO 1618 | Brassinosteroids |
| α-Pinene | Alar | BHA |
| Trans-cinnamic acid | 4-amino-5-Hexynoic acid | BHT |
| Cambrene A | Phenylethanolamine | OTA |
| Verticillene | Phenethylamine | |
| Verticillol | Glyphosphate | |
| Camphor | Dihydrocycloeucalenol | |
| Quercetin | Methionine Sulfoxide | |
| Levulinic acid | β-hydroxyphenthylanine | |
| Abietic acid | 5-Methyl-DL-Tryptophane | |
| Borneol | α-Fluorophenylalanine | |
| | 5-2 Aminoethyl-L-cysteine hydrochloride | |

TABLE 2

Components (mg/l) of Phyton Catalytic media used for cultivation of Taxus cultures.

| CHEMICAL INGREDIENT | A mg/L | B mg/L | C mg/L | D mg/L | E mg/L | F mg/L | G mg/L | H mg/L |
|---|---|---|---|---|---|---|---|---|
| Ammonium Nitrate | — | — | — | — | — | 400.0 | 500 | 400.0 |
| Ammonium Sulfate | 134.0 | — | 33.5 | 134.0 | 67.0 | — | 134.0 | — |
| Boric Acid | 3.0 | 1.5 | 0.75 | 3.0 | 1.5 | 0.75 | 6.2 | 1.5 |
| Calcium Chloride (anhydrous) | 113.24 | — | 28.31 | 113.24 | 56.62 | 72.5 | 113.24 | 72.5 |
| Calcium Chloride $2H_2O$ | — | 20.0 | 50.0 | — | — | — | — | — |
| Calcium Nitrate $4H_2O$ | — | 208.4 | — | — | — | 386.0 | — | 386.0 |
| Cobalt Chloride $6H_2O$ | 0.025 | — | 0.006 | 0.025 | 0.0125 | — | 0.025 | — |
| Cupric Sulfate $5H_2O$ | 0.025 | 0.01 | 0.006 | 0.025 | 0.0125 | 0.25 | 0.025 | 0.25 |
| $Na_2$ EDTA $2H_2O$ | 37.3 | — | 9.32 | 37.3 | 18.65 | 37.3 | 37.3 | 37.3 |
| Ferric Sulfate | — | 2.5 | — | — | — | — | — | — |
| Ferrous Sulfate $7H_2O$ | 27.8 | — | 6.95 | 27.8 | 13.9 | 27.8 | 27.8 | 27.8 |
| Magnesium Sulfate anhydrate | 122.09 | 366.2 | 30.5 | 122.09 | 61.04 | 180.7 | 122.09 | 180.7 |
| Manganese Sulfate $H_2O$ | 10.0 | 23.788 | 22.5 | 10.0 | 5.0 | 22.3 | 10.0 | 22.3 |
| Molybdenum Trioxide | — | 0.001 | — | — | — | — | — | — |
| Molybdic Acid (sodium Salt) $2H_2O$ | 0.25 | — | 0.062 | 0.25 | 0.125 | 0.25 | 0.25 | 0.25 |
| Potassium Chloride | — | 65.0 | — | — | — | — | — | — |
| Potassium Iodide | 0.75 | 0.75 | 0.175 | 0.75 | 0.375 | — | 0.75 | — |
| Potassium Nitrate | 2500.0 | 80.0 | 625.0 | 2500.0 | 1250.0 | — | 2500.0 | — |
| Potassium Phosphate (monobasic) | — | — | 10.0 | — | — | 170.0 | — | 170.0 |
| Potassium Sulfate | — | — | — | — | — | 990.0 | — | 990.0 |
| Sodium Phosphate (monobasic anhydrous) | 130.5 | 16.5 | 32.62 | 130.5 | 65.25 | — | 130.5 | — |
| Sodium Sulfate | — | 200.0 | — | — | — | — | — | — |
| Zinc Sulfate $7H_2O$ | 2.0 | 3.0 | 0.5 | 2.0 | 1.0 | 8.6 | 2.0 | 8.6 |
| Myo-Inositol | 100.0 | 100.0 | 125.0 | 100.0 | 50.0 | 100.0 | 100.0 | 100.0 |
| Nicotinic Acid | 1.0 | — | 0.75 | 1.0 | 0.5 | 1.0 | 1.0 | 1.0 |
| Pyridoxine HCl | 1.0 | — | 0.25 | 1.0 | 0.5 | 1.0 | 1.0 | 1.0 |
| Thiamine HCl | 10.0 | *5.0 | 3.5 | 10.0 | 5.0 | 10.0 | 10.0 | 10.0 |
| *Glutamine | 292.8 | 146.4 | — | 292.8 | 292.8 | 1756.8 | — | 292.8 |
| *Tryptophan | — | — | — | — | — | — | — | — |
| *Phenylalanine | — | 30.0 | — | — | — | — | — | — |
| *Lysine | — | 20.0 | — | — | — | — | — | — |
| *Methionine | — | — | — | — | — | — | — | — |
| *Sodium Acetate | — | 10.0 | 10.0 | — | — | — | — | — |
| Sucrose | 10000.0 | 50000.0 | 40000.0 | 10000.0 | 10000.0 | 10000.0 | 20000.0 | 10000.0 |
| $N_6$ Benzyladenine | 0.002 | 2.0 | 2.0 | 0.002 | 0.002 | — | — | — |
| β Naphthaleneacetic Acid | 0.931 | 10.0 | — | — | — | — | 1.862 | — |
| *Ascorbic Acid | 50.0 | 100.0 | 50.0 | 100.0 | 100.0 | 100.0 | 100.0 | 100.0 |
| Picloram | — | — | — | 1.2 | 2.4 | 1.2 | — | 1.2 |
| Casein hydrolysate | — | — | 500.0 | — | — | — | 1000.0 | — |
| 6 [γγ Dimethylallylamino] Purine | — | — | — | — | — | 0.02 | — | — |
| Kinetin | — | — | — | — | — | — | — | 0.02 |
| pH | 5.6 | 5.8 | 5.8 | 5.6 | 5.6 | 5.6 | 5.6 | 5.6 |

*Filter-sterilized into autoclaved medium

TABLE 3

Preferred conditions for callus proliferation for various Taxus species. The ingredients in the basal media are listed in Table 2.

| Species | Basal Medium (Table 2) | Auxin Type | Auxin Conc (M) | Cytokinin Type | Cytokinin Conc (M) |
|---|---|---|---|---|---|
| T. brevifolia | F | P | $5 \times 10^{-6}$ | 2iP | $10^{-7}$ |
|  | D | P | $5 \times 10^{-6}$ | BA | $10^{-8}$ |
| T. canadensis | H | P | $5 \times 10^{-6}$ | K | $10^{-7}$ |
|  | D | P | $5 \times 10^{-6}$ | BA | $10^{-8}$ |
| T. chinensis | D | P | $5 \times 10^{-6}$ | BA | $10^{-8}$ |
|  | A | N | $5 \times 10^{-6}$ | BA | $10^{-8}$ |
| T. globosa | D | P | $5 \times 10^{-6}$ | BA | $10^{-8}$ |
| T. floridana | D | P | $5 \times 10^{-6}$ | BA | $10^{-8}$ |
| T. baccata | D | P | $5 \times 10^{-6}$ | BA | $10^{-8}$ |
| T. cuspidata | D | P | $5 \times 10^{-6}$ | BA | $10^{-8}$ |
| T. media | D | P | $5 \times 10^{-6}$ | BA | $10^{-8}$ |
| T. wallichiana | D | P | $5 \times 10^{-6}$ | BA | $10^{-8}$ |

*Abbreviations:
Picloram (P), Naphthalene acetic acid (N), Benzyladenine (BA), Dimethyl allylamino purine (2iP), Kinetin (K)

TABLE 4

Typical growth characteristics of Taxus sp. suspension cultures

| Species | Dry Weight Doubling Time | Fresh Weight Doubling Time | Dry Wt. Density | Fresh Wt. Density |
|---|---|---|---|---|
| T. brevifolia | 2.0 days | 3.5 days | 20 g/L | 400 g/L |
| T. baccata | 2.0 | 6.0 | 15 | 220 |
| T. chinensis | 2.5 | 4.5 | 20 | 285 |
| T. canadensis | nd* | 8.5 | 13 | 260 |

*not yet determined

TABLE 5

Taxol production in various Taxus species.

| Species | Taxol content (% dry weight) | Medium (See Tables 2 & 3) | Analysis |
|---|---|---|---|
| T. brevifolia | 0.006 | F | ELISA |
| T. canadensis | 0.004 | H | ELISA |
| T. baccata | 0.0014 | D | HPLC |
| T. globosa | 0.0003 | G | ELISA |
| T. cuspidata | 0.0025 | G | HPLC |
| T. floridana | 0.001 | G | ELISA |
| T. media | 0.02 | F | ELISA |
| T. chinensis | 0.18 | B | HPLC |

TABLE 6

Improvements in productivity due to medium exchange treatment. Numbers are expressed as X-fold improvement over levels achieved in a 15-day batch interval. *Taxus chinensis* cell line K-1 was cultivated in Medium A in the dark.

|  | Total levels* | Extracellular levels |
|---|---|---|
| Taxol | 4.6 | 4.89 |
| Total taxanes | 4.55 | 5.94 |

*Total levels in cells and medium combined

TABLE 7

Effect of Standard GroLux light treatment on taxol and taxane content in 10-day old cultures of *Taxus chinensis* line K-1 cultivated in Medium A. Amounts shown are expressed as μg extracted from 20 ml of suspension. Cell growth was identical in both treatments (164 mg dry weight per flask).

|  | Light | Dark |
|---|---|---|
| Total taxol: cells and medium: | 8.8 μg | 3.13 μg |
| Extracellular taxol: | 76.40% | 56.20% |
| Total taxanes cells and medium: | 61.55 μg | 62.17 μg |
| Extracellular taxanes: | 89% | 84% |

TABLE 8

Comparison of chitosan-glutamate treated to non-elicited suspensions of *Taxus chinensis* line K-1 after 15 day cultivation in medium C. Taxane levels reported are from cells and medium combined. % extra refers to the percentage of extracellular product.

| Taxanes | CONTROL | | | ELICITOR | | |
|---|---|---|---|---|---|---|
|  | Cell density 10.1 g/L | | | Cell density 14.2 g/L | | |
|  | Cell viability 70–80% viable | | | Cell viability 75–80% viable | | |
|  | % dry wt | mg/L | % Extra | % dry wt | mg/L | % Extra |
| Taxol | 0.054 | 5.4 | 72.0 | 0.098 | 13.9 | 85.0 |
| Baccatin III | 0.057 | 5.8 | 69.9 | 0.055 | 7.8 | 76.6 |
| 7-Xylosyl-10-deacetyltaxol | 0.040 | 4.0 | 63.0 | 0.048 | 6.9 | 77.0 |
| 10-deacetyltaxol | 0.004 | 0.4 | 71.1 | 0.0 | 1.0 | 75.3 |
| Cephalomannine | | | | | | |
| 10-deacetylbaccatin III | | | | | | |
| 10-deacetyl-7-epitaxol | 0.054 | 5.4 | 74.2 | 0.076 | 10.8 | 85.7 |
| 7-Epitaxol | 0.009 | 0.9 | 74.6 | 0.009 | 1.3 | 86.2 |
| Unknown Taxanes | 0.203 | 20.5 | 79.7 | 0.240 | 34.1 | 90.2 |
| Total Taxanes: | 0.421 | 42.4 | | 0.533 | 75.8 | |

TABLE 9

Nutrient medium manipulation for enhanced taxane and taxol biosynthesis in *Taxus chinensis* suspension line K-1. 500 mg fresh weight cells were inoculated per 5 mL of medium and incubated in the dark for 18 days. The total taxanes produced (in the cells and medium combined) is reported. The ingredients in media B & C are listed in Table 2.

| Taxane Level | Medium B (mg/L) | Medium C (mg/L) |
|---|---|---|
| Baccatin III | 4.3 | 3.9 |
| 7-xylosyl 10-deacetyl taxol | 8.3 | 12.9 |
| Cephalomannine | 1.1 | trace |
| 10-deacetyl 7-epi taxol | 4.6 | 5.4 |
| taxol | 24.1 | 21.3 |
| 7-epi taxol | 1.3 | 2.8 |
| other unidentified taxanes* | 56.1 | 63.7 |
| Total taxanes | 99.8 mg/l | 110 mg/l |

What is claimed is:

1. A process for recovering taxol and taxanes in high yield from cell cultures of *Taxus chinensis*, comprising:
   (a) cultivating in one or more nutrient media cells derived from a callus cell culture or suspension cell culture, or both, of *Taxus chinensis*, to form a cell culture under growth and product formation conditions to produce taxol in an amount of at least 10-fold greater than that produced by native *Taxus chinensis*, and taxanes;
   (b) recovering said taxol, in an amount at least 10-fold greater than that produced by native *Taxus chinensis*, and taxanes, from cells, media or cells and media of said cell culture.

2. A process for recovering taxol and taxanes in high yield from cell cultures of *Taxus chinesis*, comprising:
   (a) culturing in one or more nutrient media, cells derived from *Taxus chinensis* under conditions to produce taxol, in an amount at least 10-fold greater than that produced by native *Taxus chinensis*, and taxanes, said culturing comprising:
   (i) inoculating *Taxus chinensis* cells into growth and maintenance nutrient medium (1) in suspension to form an inoculated suspension;
   (ii) cultivating said inoculated suspension of Step (i) to form a suspension culture;
   (iii) subculturing said suspension culture of Step (ii) into production nutrient medium (2) to form said production culture; and
   (iv) cultivating said production culture of Step (iii) under conditions to produce taxol and taxanes; and
   (b) recovering said taxol, in an amount at least 10-fold greater than that produced by native *Taxus chinensis*, and taxanes from media, cells, or media and cells of said production culture of Step (iv).

3. The process of any one of claims 1 or 2, wherein said taxol is produced in an amount of at least 35-fold greater than that produced by native *Taxus chinensis*.

4. The process of any one of claims 1 or 2, wherein cultures are cultivated in continuous or intermittent broad band or narrow band light.

5. The process of any one of claims 1 or 2, wherein nutrient medium comprise one or more members selected from the group consisting of: a carbohydrate and any other carbon source or inorganic and organic nitrogen sources.

6. The process of any one of claims 1 or 2, wherein nutrient medium comprise one or more members selected from the group consisting of: a macrosalt, a microsalt, a rare trace element, and a vitamin and other organic supplements.

7. The process of any one of claims 1 or 2, wherein nutrient media comprise one or more members: selected from the group consisting of: a plant hormone, a hormone substitute, a hormone derivative, a hormone inhibitor and a synthetic growth regulator.

8. The process of any one of claims 1 or 2, wherein nutrient medium comprise one or members selected from the group consisting of: a biosynthetic precursor, a metabolic inhibitor, a non-metabolic inhibitor, a stimulant, and an activator.

9. The process of any one of claims 1 or 2, wherein nutrient media comprise one or more members selected from the group consisting of: an anti-browning agent, an anti-oxidant, a stabilizer, an enhancer, a radical scavenger, a conditioner and a reducing agent.

10. The process of claim 1, wherein said one or more nutrient media comprise a growth and maintenance nutrient medium (1) and a production nutrient medium (2).

11. The process of any one of claims 1 or 2, where said growth and maintenance nutrient medium (1) and said production nutrient medium (2) are different.

12. The process of any one of claims 1 or 2, wherein said growth and maintenance nutrient medium (1) and said production nutrient medium (2) are the same.

13. The process of any one of claims 1 or 2, wherein said cultivating in said production nutrient medium (2) is carried out for up to 42 days.

14. The process of any one of claims 1 or 2, further comprising periodic taxol or taxane removal and periodic medium exchange.

15. The process of any one of claims 1 or 2, wherein growth and product formation are achieved using a process selected from the group consisting of: a one-stage batch process, a two-stage process, a fed-batch process, a semi-continuous process, and a continuous process.

16. The process of any one of claims 2 or 10, wherein said production nutrient medium (2) comprises one or more members selected from the group consisting of: a biotic elicitor and an abiotic elicitor.

17. The process of claim 16, wherein said biotic elicitor is chitosan glutamate.

18. The process according to claim 2, wherein said growth and maintenance nutrient medium (1) of step (a)(i) comprises an anti-browning agent.

* * * * *

UNITED STATES PATENT AND TRADEMARK OFFICE
CERTIFICATE OF CORRECTION

PATENT NO. : 5,407,816
DATED : April 18, 1995
INVENTOR(S) : Bringi, et al.

It is certified that error appears in the above-indentified patent and that said Letters Patent is hereby corrected as shown below:

In column 6, lines 10 and 11, replace "Chlorox" with --CLOROX-- in both occurrences.

In column 11, line 45, replace "Chlorox" with --CLOROX--.

In Table 1.a. in column 20-22, replace

"*Pythium mamiallatum*" with --*Pythium mamillatum*--,

"*Colletotrichum orbiculum*" with --*Colletotrichum orbiculare*--,

"*Leptosphaeria torrae*" with --*Leptosphaeria korroae*--,

"*Venturia inequalis*" with --*Venturia inaequalis*--,

"Dibutyrl Cyclic AMP" with --Dibutyryl Cyclic AMP--

"Methyl Jasmone" with --Methyl Jasmonate--,

"Nordihydroguairetic acid" with --Nordihydroguaiaretic acid--, and

"d-amino-DL-Phenylalanine" with β-amino DL-Phenylalanine--,

"Diazolidenyl urea" with --Diazolidinyl urea".

UNITED STATES PATENT AND TRADEMARK OFFICE
CERTIFICATE OF CORRECTION

PATENT NO. : 5,407,816
DATED : April 18, 1995
INVENTOR(S) : Bringi, et al.

It is certified that error appears in the above-indentified patent and that said Letters Patent is hereby corrected as shown below:

In Table 1.b. in column 21-22, replace

"Tryptophane" with --Tryptophan--,

"Glyphosphate" with --Glyphosate--,

"β-hydroxyphenethylanine" with --β-hydroxyphenethylamine--,

"5-Methyl-DL-Tryptophane" with --5-Methyl-D, L-Tryptophan--

"Dibutyrl Cyclic AMP" with --Dibutyryl Cyclic AMP--, and

"Methyl Jasmone" with --Methyl Jasmonate--.

Signed and Sealed this

Twenty-fifth Day of March, 1997

Attest:

BRUCE LEHMAN

*Attesting Officer*  *Commissioner of Patents and Trademarks*

UNITED STATES PATENT AND TRADEMARK OFFICE
CERTIFICATE OF CORRECTION

PATENT NO. : 5,407,816
DATED : April 18, 1995
INVENTOR(S) : BRINGI et al.

It is certified that error appears in the above-identified patent and that said Letters Patent is hereby corrected as shown below:

Col. 26, line 53
In claim 5, replace "nutrient medium" with --the one or more nutrient media--.

Col. 26, line 58
In claim 6, replace "nutrient medium" with --the one or more nutrient media--.

Col. 26, line 63
In claim 7, replace "nutrient media" with --the one or more nutrient media--, and replace "members:" with --members--.

Col. 26, line 68
In claim 8, replace "nutrient medium" with --the one or more nutrient media--, and replace "one or members" with --one or more members--.

Col. 27, line 6
In claim 9, replace "nutrient media" with --the one or more nutrient media--.

Signed and Sealed this

Ninth Day of March, 1999

Attest:

Q. TODD DICKINSON

Attesting Officer

Acting Commissioner of Patents and Trademarks